(12) United States Patent
Verboven et al.

(10) Patent No.: US 10,318,515 B2
(45) Date of Patent: Jun. 11, 2019

(54) METHOD AND SYSTEM FOR PROVIDING A CLARITY GRADE FOR A GEM

(71) Applicant: GEMOLOGICAL INSTITUTE OF AMERICA, INC. (GIA), Carlsbad, CA (US)

(72) Inventors: Marc Verboven, Vloeiende (BE); Troy Blodgett, Flagstaff, AZ (US)

(73) Assignee: GEMOLOGICAL INSTITUTE OF AMERICA, INC. (GIA), Carlsbad, CA (US)

( * ) Notice: Subject to any disclaimer, the term of this patent is extended or adjusted under 35 U.S.C. 154(b) by 0 days.

(21) Appl. No.: 15/151,902

(22) Filed: May 11, 2016

(65) Prior Publication Data

US 2017/0046372 A1    Feb. 16, 2017

Related U.S. Application Data

(63) Continuation of application No. 13/845,995, filed on Mar. 18, 2013, now Pat. No. 9,366,638, which is a continuation of application No. 12/287,187, filed on Oct. 7, 2008, now Pat. No. 8,402,066.

(51) Int. Cl.
*G06F 7/00* (2006.01)
*G06F 16/22* (2019.01)
*G01N 21/87* (2006.01)

(52) U.S. Cl.
CPC ......... *G06F 16/2282* (2019.01); *G01N 21/87* (2013.01)

(58) Field of Classification Search
CPC ............. G06F 17/30339; G06F 1/1656; G06F 1/1658; G06F 2203/04109; G01N 21/87

USPC .......................................... 707/802, 688, 700
See application file for complete search history.

(56) References Cited

U.S. PATENT DOCUMENTS

| | | | | |
|---|---|---|---|---|
| 5,615,005 A * | 3/1997 | Valente | ................. | G01J 3/0251 356/30 |
| 5,950,178 A * | 9/1999 | Borgato | ................. | G06Q 30/06 705/35 |
| 6,020,954 A * | 2/2000 | Aggarwal | .............. | G01N 21/87 356/30 |
| 7,652,755 B2 * | 1/2010 | Liu | ........................ | G01N 21/87 250/228 |
| 8,515,150 B2 * | 8/2013 | Mangoubi | ............ | G06K 9/0014 382/133 |

(Continued)

*Primary Examiner* — Mohammed R Uddin
(74) *Attorney, Agent, or Firm* — DLA Piper, LLP (US)

(57) ABSTRACT

A method and system for generating a clarity grading look-up table includes collecting actual inclusion parameter data for a plurality of gems, where the actual inclusion parameter data includes an actual clarity grade and an actual inclusion parameter data combination. A mathematical relationship between a clarity grade and a particular inclusion parameter combination is then extrapolated from the actual inclusion parameter data. A derived clarity grade is then assigned to a plurality of inclusion parameter combinations as a function of the mathematical relationship and a set of inputted inclusion parameters. Also, a method and system for providing a clarity grade includes receiving a plurality of inclusion characteristics associated with a gem and parameterizing each of the inclusion characteristics, so that a parameter value is assigned to each inclusion characteristic. The parameter values are then input to a mathematical formula so as to provide a parameterized clarity grade for the gem.

9 Claims, 15 Drawing Sheets

(56) References Cited

U.S. PATENT DOCUMENTS

| | | | |
|---|---|---|---|
| 8,639,479 B2* | 1/2014 | Sivovolenko | G01N 21/87 345/420 |
| 2004/0051861 A1* | 3/2004 | Bray | A44C 17/00 356/30 |
| 2006/0048024 A1* | 3/2006 | Lidin | G01R 31/31813 714/724 |
| 2006/0074588 A1* | 4/2006 | Blodgett | A44C 17/001 702/179 |
| 2006/0164623 A1* | 7/2006 | Wagner | G01N 21/87 356/30 |
| 2006/0190292 A1* | 8/2006 | Reinitz | G01N 21/87 356/30 |
| 2006/0267975 A1* | 11/2006 | Moses | G06T 11/206 345/419 |
| 2007/0067178 A1* | 3/2007 | Reinitz | G01N 21/87 705/306 |
| 2007/0186918 A1* | 8/2007 | Ceulemans | A44C 17/00 125/30.01 |
| 2009/0319336 A1* | 12/2009 | Mehta | G06Q 30/02 705/7.35 |
| 2010/0141929 A1* | 6/2010 | Liu | G01N 21/87 356/30 |

* cited by examiner

WORKSHEET CLARITY GRID

ID Number:

Control Number:        Grader:                    Date:

Weight:

Diameter or Width:          Length:

Shape:            RBC  -  MQ  -  PE  -  OV  -  EM  -  CC  -  REC  -  OTHER

Clarity Grade Diamond:   IF  -  VVS1  -  VVS2  -  VS1  -  VS2  -  SI1  -  SI2  -  I1  -  I2  -  I3

HIGH              -        MEDIUM        -         LOW

| MAGNIFICATION: | INCLUSION 1 | INCLUSION 2 | INCLUSION 3 |
|---|---|---|---|
| Size | | | |
| Length | | | |
| Long | | | |
| Clarity Grade | | | |
| High – Medium – Low | | | |
| Internal | | | |
| Surface Reaching | | | |
| Position | | | |
| Number | | | |
| Nature | | | |
| Relief White | | | |
| Relief Black | | | |
| Observation Direction | | | |
| Depth | | | |

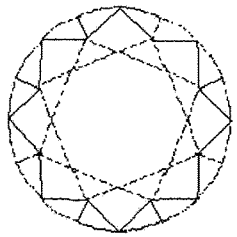 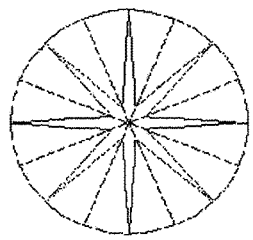 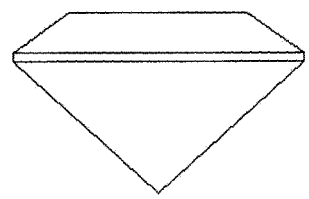

| Remarks | | | |
|---|---|---|---|

CLARITY gaps crystals data base

| Inclusion Size Percentage | | Relief White 1 | | | | Relief White 2 | | | | Relief White 3 | | | | Relief White 4 | | | | Relief White 5 | | | |
|---|---|---|---|---|---|---|---|---|---|---|---|---|---|---|---|---|---|---|---|---|---|
| | | T | T/Cr | Cr | G | T | T/Cr | Cr | G | T | T/Cr | Cr | G | T | T/Cr | Cr | G | T | T/Cr | Cr | G |
| VVS | 1 +2 | | | | | | | | | | | | | | | | | | | | |
| | 1 | 8 | 1 | | | 43 | 15 | | | | | | | | | | | | | | |
| | 2 | | | 1 | | | | 23 | 8 | 64 | 18 | 30 | 10 | 28 | 4 | 8 | | | | | |
| VS | | 5 | | 3 | | 61 | 23 | 23 | 9 | 46 | 16 | 23 | 4 | 24 | 2 | 5 | 1 | | | 1 | 3 |
| | 1 | 5 | | | | 44 | 8 | 19 | 1 | 46 | 11 | 20 | 4 | 4 | 2 | 1 | 1 | 1 | | 1 | |
| SI | 2 | 3 | 3 | 1 | | 21 | 4 | 5 | | 21 | 5 | 8 | | 5 | | | | | | 1 | |
| | 1 | 1 | | 1 | | 9 | 1 | 1 | | 13 | 7 | 2 | | 1 | | | | | | | |
| I | 2 | | | | | 1 | | 1 | | 1 | | 1 | | | | | | | | | |
| | 3 | | | | | | | | | | | | | | | | | | | | |

Entry 810
Gap 820

Fig. 8A

CLARITY gaps feathers data base

| Inclusion Size Percentage | Relief White 1 | | | | Relief White 2 | | | | Relief White 3 | | | | Relief White 4 | | | | Relief White 5 | | | |
|---|---|---|---|---|---|---|---|---|---|---|---|---|---|---|---|---|---|---|---|---|
| | T | T/Cr | Cr | G | T | T/Cr | Cr | G | T | T/Cr | Cr | G | T | T/Cr | Cr | G | T | T/Cr | Cr | G |
| VVS 1+2 | | | | | | | | | | | | | | | | | 1 | | | |
| 1 | | | | | 1 | | | | | | 1 | | | | 1 | 2 | | | | 3 |
| 2 | 1 | | | | 4 | 1 | 1 | 1 | 1 | | 2 | 2 | 3 | 1 | 1 | 7 | 3 | 1 | 5 | 6 |
| VS 1 | 1 | 1 | | | 12 | 4 | 4 | 8 | 5 | 11 | 12 | 13 | 5 | 6 | 12 | 19 | 1 | 2 | 5 | 1 |
| 2  ← Entry 830 | | | 2 | 1 | 4 | 3 | 21 | 28 | 10 | 7 | 33 | 27 | 10 | 5 | 8 | 15 | 1 | 1 | 3 | |
| 1  ← Gap 840 | 2 | 1 | 1 | 2 | 9 | 8 | 25 | 29 | 15 | 3 | 16 | 28 | 1 | 3 | 3 | | 1 | | 1 | |
| 2 | 4 | 4 | 10 | 1 | 2 | 7 | 29 | 10 | 4 | 1 | 5 | 10 | | | | | | | | |
| 3 | | 1 | 6 | | 3 | | 19 | 1 | 3 | | 2 | | | | 1 | | | | | |
| I 1 | | | 2 | | | 1 | 6 | | 2 | | | | | | | | | | | |

Fig. 8B

METHOD AND SYSTEM FOR PROVIDING A CLARITY GRADE FOR A GEM

This application is a continuation of application Ser. No. 13/845,995, filed on Mar. 18, 2013, which in turn is a continuation of application Ser. No. 12/287,187, filed Oct. 7, 2008 and issued as U.S. Pat. No. 8,402,066, each of which is incorporated by reference herein by its entirety.

TECHNICAL FIELD

The present invention is directed generally towards analyzing a gem, and more specifically towards parameterizing aspects of the clarity grading process for a gem and forming a clarity grading model and look-up table for use in clarity grading of a gem.

BACKGROUND OF THE TECHNOLOGY

All experienced diamond graders understand that clarity grades can differ because of any number of inclusion characteristics. Such differences may, for example, include differences in an inclusion's size, type, position or relief (i.e., brightness). However, graders generally cannot describe exactly how much each characteristic actually influences the ultimate clarity grade. Instead, graders mostly rely on their diamond grading training and experience to provide them with a memory of visual references with which to evaluate each new case individually. For example, to ascertain how a SI1 inclusion located near the girdle would be graded if it were located in the center of the table, or how a VS2 inclusion with a Low relief would be graded if it had a High relief instead, is nearly impossible for a grader to do without concrete examples to refer to. In many situations, extensive reliance on concrete examples, however, is impractical since it would be difficult, expensive, and impracticable to obtain concrete examples of every possible inclusion characteristic combination. Consequently, the clarity grading process is vulnerable to the grader subjectivities, which can affect the consistency of clarity grades in the field.

In view of the need for consistency and uniformity in the clarity grading process, developing tools that could more objectively, and preferably mathematically, predict the influences of particular inclusion characteristics on clarity grade would be extremely helpful. Such tools, may then be used to better understand the visual clarity grading decision processes, and to help provide consistency in these processes by providing these tools to grader trainees uniformly. Accordingly, there is currently a need for an improved method and system for providing a clarity grade for a gem.

SUMMARY OF THE INVENTION

This invention addresses the aforementioned problems by providing an improved method and system for providing a clarity grade for a gem.

In an embodiment of the present invention, a method is provided for generating a look-up table for use in clarity grading a gem. The method comprises collecting actual inclusion parameter data and an associated clarity grade for each of a plurality of gems. From the actual inclusion parameter data and the associated clarity grades, mathematical relationships are derived which model interactions between clarity grades and combinations of inclusion parameters. Parameterized clarity grades are then associated with corresponding combinations of inclusion parameter value ranges based upon the derived mathematical relationships, so that for a set of input inclusion parameter values, a corresponding parameterized clarity grade is provided.

In another embodiment of the present invention, a method for generating a clarity grading look-up table is provided which comprises obtaining actual inclusion parameter data for a plurality of gems, wherein the actual inclusion parameter data for each gem includes an actual clarity grade associated with a combination of inclusion parameters represented by the actual inclusion parameter data; deriving from the actual inclusion parameter data mathematical relationships relating to the influence of interacting inclusion parameter combinations on clarity grades; and populating a table with a plurality of clarity grade designations associated with combinations of ranges of inclusion parameter values as defined by the mathematical relationships.

In a further embodiment of the present invention, a method is provided for determining a clarity grade for a gem. The method includes receiving a plurality of inclusion characteristics associated with a gem. Each of the plurality of inclusion characteristics are parameterized to have corresponding inclusion parameter values. The corresponding inclusion parameter values are evaluated in accordance with a mathematical relationship which models the relative influence of inclusion parameter values upon clarity grade, and which is selected as a function of the inclusion parameter values. Provided as the clarity grade for the gem is a parameterized clarity grade based upon the evaluation of the inclusion parameter values in accordance with the selected mathematical relationship.

In another embodiment of the invention, a computer-readable medium having computer-executable instructions thereon for rendering digital content on a device is provided. Within such embodiment, the computer-readable medium includes a first, second, and third module. The first module provides instructions for receiving actual inclusion parameter data for a plurality of gems. The actual inclusion parameter data for each gem includes an actual clarity grade and an actual inclusion parameter data combination. The second module provides instructions for deriving a mathematical relationship between a clarity grade and a particular inclusion parameter combination. For this embodiment, the mathematical relationship is derived from the actual inclusion parameter data. The third module provides instructions for assigning a derived clarity grade to each of a plurality of inclusion parameter combinations, such that the derived clarity grade is a function of the mathematical relationship and a set of inputted inclusion parameters.

In a further embodiment of the invention, another method for generating a clarity grading look-up table is provided. Within such embodiment, the method includes the step of obtaining actual inclusion parameter data for a plurality of gems. The actual inclusion parameter data for each gem includes an actual clarity grade and an actual inclusion parameter data combination. The method also includes the step of deriving a mathematical relationship between a clarity grade and a particular inclusion parameter combination. For this embodiment, the mathematical relationship is derived from the actual inclusion parameter data. The method also includes the step of populating a table with a plurality of derived clarity grades, such that each derived clarity grade is a function of the mathematical relationship and a particular set of inputted inclusion parameters.

In yet another embodiment of the invention, another computer-readable medium having computer-executable instructions thereon for rendering digital content on a device is provided. Within such embodiment, the computer-readable medium includes a first, second, third, and fourth module. The first module provides instructions for receiving a plurality of inclusion characteristics associated with a gem. The second module provides instructions for parameterizing each of the plurality of inclusion characteristics, so that a parameter value is assigned to each of the plurality of inclusion characteristics. The third module provides instructions for inputting the parameter value for each of the plurality of inclusion characteristics into a mathematical formula. And finally, the fourth module includes instructions for providing a parameterized clarity grade for the gem, where the parameterized clarity grade is an output of the mathematical formula.

As will be appreciated upon consideration of the following detailed description of the invention and accompanying drawings, there are many advantages and features of the present invention, which in turn lead to many new and useful applications of the invention.

BRIEF DESCRIPTION OF THE DRAWINGS

FIG. 4 is an exemplary worksheet clarity grid according to an embodiment of the invention.

FIG. 5 is an exemplary table summarizing characteristics and/or parameters of inclusions for a collection of different diamonds assembled in accordance with an embodiment of the invention.

FIG. 6 is an exemplary input form for entering inclusion characteristics into a data base according to an embodiment of the invention.

FIG. 7 is an exemplary page showing query results for a particular combination of inclusion parameters according to an embodiment of the invention.

FIG. 8A is mapping distribution identifying data gaps for crystal inclusions used in the collecting of inclusion parameter and clarity grade data according to an embodiment of the invention.

FIG. 8B is mapping distribution identifying data gaps for feather inclusions used in the collecting of inclusion parameter and clarity grade data according to an embodiment of the invention.

DETAILED DESCRIPTION OF THE INVENTION

Figure 1:
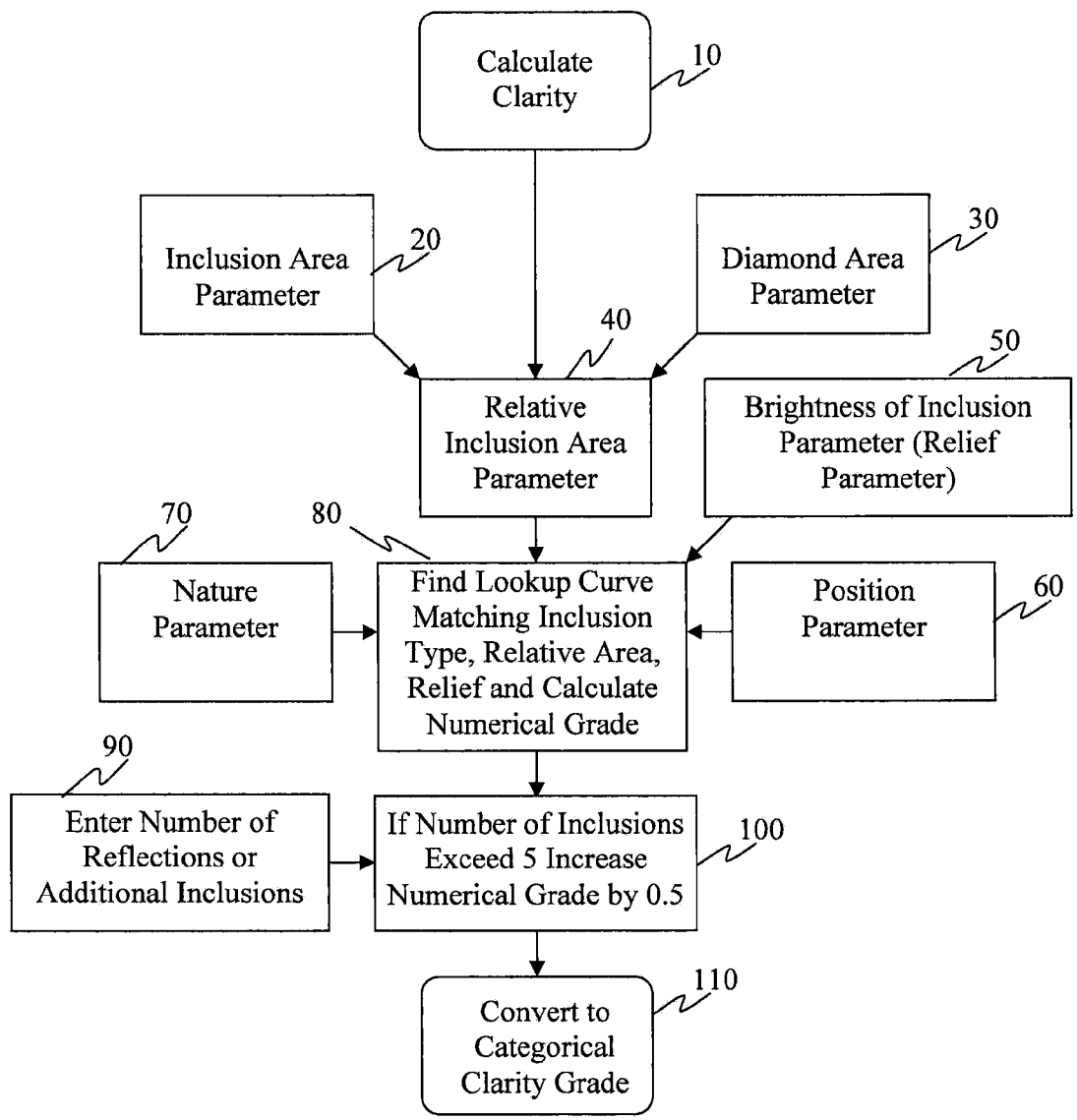
FIG. 1 is a flow chart for providing a clarity grade according to an embodiment of the invention.

The present invention is directed towards providing a method and system for providing a clarity grade for a gem in which inclusion parameters are quantified rather than simply categorized into verbal descriptions (e.g., such as "Very Small" (VS) in size). More specifically, the present invention applies a new approach to visual clarity grading by first identifying and correlating the influences which determine the visual clarity grade of a diamond, particularly the range from "very very small" (VVS) to "heavily included diamonds," and then breaking down clarity grades into separate yet interacting inclusion parameters. Moreover, the parameter combinations that influence the clarity grade are broken down into individual inclusion parameters whose additive properties form predictable relationships. As a result, numerical upper and lower limits for each of a plurality of parameter combinations may be defined in order to translate measured and/or parameterized values into a particular clarity grade.

Although any of several inclusion characteristics may influence the ultimate clarity grade of a gem, a few characteristics have been identified to be particularly influential. Namely, the size, position, relief, number, and type of a gem's inclusions have been identified. Accordingly, a brief description of each is provided below, along with a discussion of their respective significance.

The size of an inclusion has the strongest overall impact on the clarity grade and the larger the inclusion, the greater the impact. The size of an inclusion is preferably represented in the face-up view of a diamond, for example, as a two dimensional object. The length and width of a two dimensional inclusion can be measured directly with a microscope equipped with a measuring graticule. An equation for an ellipse may then be fed these measurements and used to approximate the inclusion area. Although a certain degree of error is associated with this approximation, which is higher for irregularly shaped inclusions, with a sufficient quantity of data, errors can be smoothed out to produce general relationships that can be used to predict the influence of the face-up area of an inclusion on the clarity grade. This elliptical approximation of inclusion area has been validated by obtaining similar results with a digital imaging analysis application using a more precise method which digitizes the outline of the inclusion, counts the number of pixels inside the outline, and then converts the number of pixels into an inclusion size area or area relative to the size of the diamond. Inclusion size may also be obtained using the techniques of this digital imaging analysis application. A more detailed description of this digital imaging analysis application is provided in U.S. patent application Ser. No. 12/287,186, entitled "An Automated System And Method For Clarity Measurements And Clarity Grading," filed even date herewith, and incorporated herein by reference in its entirety (hereafter, "Clarity Measurement Application").

An important aspect of the inclusion size parameter analysis is the conversion of the area of the inclusion into a ratio of the inclusion area to the size of the diamond. Although most graders would agree that similarly sized inclusions should not equally impact a 1.0 ct stone versus a 10.0 ct stone, diamond graders cannot explain or predict, in a hypothetical sense, how the size of the diamond will influence the results. They must first see an example and visually compare the inclusion size to the size of the diamond in order to confidently provide a clarity grade. In contrast, as will be described in this application, by establishing numerical relationships in accordance with an embodiment of the present invention, one can predict the inclusion size parameter influence on the clarity grade without visual examination. The inclusion size parameter can be calculated, as described in the Clarity Measurement Application, by the summing of all the pixels within the inclusion area that are isolated by a script. Then a calculation can be made to find the inclusion area size relative to the size of the diamond area (the calculation of which is based on the diameter). Such information, in accordance with an embodiment of the invention, can then be used with information about other inclusion parameters of the gem to predict clarity grade of the gem.

The positioning of an inclusion can also influence the final clarity grade of a gem since an inclusion's position affects its visibility. Inclusions located just under the table (sometimes referred to as the "heart"), for example, are generally much more visible than similar inclusions located under the bezel facets or near the girdle. Also, although an inclusion might be small and located in an inconspicuous place, if it is reflected in the pavilion facets, it may look like many inclusions, not just one. When this happens, it is called a reflector, which generally tends to lower the clarity grade more than similar, non-reflecting inclusions. In practice, a grader may thus view and classify one of two inclusions differently even if both inclusions are of similar relative sizes depending on their position parameter. There are two main explanations for this. First, there is a tendency for an inclusion to be more visible when it is located towards the center of the diamond (and thus also closer to the center of an observer's attention) as opposed to a location closer to the girdle. A second explanation is that a more explicit facet distribution and facet reflection pattern toward the edge of most diamonds may tend to hide inclusions, and reduce their visibility, making them less important.

One feature of an embodiment of the present invention is the parameterization of inclusion characteristics, that is a categorizing of inclusions or other clarity characteristics so that such characteristics can be described, collected and analyzed in a consistent way. In connection with a location mapping operation, position identification guidelines were developed by which the positions (locations) of inclusions may be parameterized. The inclusion position parameter may be a pixel-based parameter obtained using a mapping feature of the imaging software, or an operator supplied set of information. In accordance with a preferred parameterization approach, the inclusions are sorted into locations defined as pavilion, girdle, crown, table-crown, and table. These locations will be described in greater detail hereafter in connection with FIG. 3A. When the inclusion position parameter is pixel-based, the precise location of the inclusion may, for example, be determined by the digital gravity point of the inclusion's pixels.

A gem's relief refers to its visibility and is used in accordance with an embodiment of the invention as a categorical measure of the contrast between the inclusion and the surrounding facet distribution and reflection pattern of a diamond. As a general rule, the brighter an inclusion is, the more visible an inclusion appears to be to the grader who may lower the clarity grade as a result. Most inclusions are white or colorless, but some can be black, brown, dark red, or green. The dark inclusions are usually easier to see, so they have a greater impact on the clarity grade than the colorless inclusions.

To determine an inclusion's relief parameter, techniques described in the Clarity Measurement Application may again be used, wherein a pixel histogram of the inclusion may be measured relative to the histogram of an area proximate to the inclusion. The relief of the inclusion is then determined by matching the relationship between the two histograms to one of a set of reference images with known relief factors. Alternatively, the relief of an inclusion may be calculated from pixilated image data by using the ratio of the average pixel value within the inclusion to the average pixel value of an area of the image with a constant radius surrounding the inclusion.

Generally, although the number of inclusions has been found to have a minor role in influence clarity grade, a sufficient quantity of additional inclusions of similar size or reflections of inclusions can typically lower the clarity grade by a half a grade. As previously mentioned, additional inclusions may appear as face-up reflections of inclusions, or mirror images, which can look like additional inclusions to an observer and are therefore graded the same as additional inclusions. Also, depending on the location of an inclusion in a diamond, the distribution of facets can cause the inclusion to appear multiple times or be reflected, especially when the inclusion is positioned deep and near the culet of the diamond. Notwithstanding the reason(s) why additional inclusions are viewed, a parameter which accounts for the number of inclusions may be included via an automatic correction factor for reflections and/or manually to account for the total number of inclusions.

The type of a diamond's inclusions also influences its clarity grade. Clarity characteristics, according to their type, may be divided into two categories: internal and surface-reaching inclusions. Although each of these categories may be further subdivided according to particular clarity grading procedures, the more common clarity characteristics for type are whether the inclusions are crystals or feathers. Large breaks in the stone, or feathers, are potentially hazardous, especially if they reach the table or extend from the crown through the girdle. If present, feathers typically have a lesser impact on the clarity grade than crystals. In accordance with an embodiment of the present invention, because of the predominance of crystals and feathers, the type parameter may be defined in terms of crystal and feather inclusions with these more common clarity characteristics serving as proxies for some of the rarer types of inclusions. The actual type parameter may be entered manually by an operator.

Another variable that can have an influence on the final clarity grade result is the durability. This is almost never applicable to internal clarity characteristics, but surface reaching clarity characteristics can occasionally pose a degree of risk of further breakage or chipping and lower the final clarity grade call. As such, in accordance with an embodiment of the invention, parameters for High, Medium, or Low durability risk factors may be considered. Here, however, the scarcity of High and Medium examples has limited efforts to develop a predictive influence of such a durability parameter on the clarity grade. Nevertheless, one of ordinary skill in the art would appreciated that including such a parameter would still be within the scope and spirit of the present invention.

By quantifying inclusion characteristics or parameters, such as those described above, predictable relationships for particular parameter combinations may thus be used to provide a parameterized clarity grade. An exemplary flow chart of how to provide such a parameterized clarity grade, according to an embodiment of the invention, is provided in FIG. 1, using a diamond as an example. For this particular embodiment, although the characteristics of size, position, relief, number, and type of a gem's inclusions are used, it should be appreciated that these characteristics are used solely for exemplary purposes and that other embodiments may include any of a plurality of inclusion characteristic combinations, including characteristics not mentioned here. It should also be noted that the grade setting inclusions were focused upon in developing the primary inclusion parameter relationships, while the number of inclusions and reflections were considered together as an additional influence on the clarity grade. Also, as discussed hereinafter, the relief parameter was consolidated from initially five categories into only three (i.e., High, Medium and Low), and other selections were made in specifying how inclusions characteristics may be parameterized in accordance with various embodiments of the invention.

As illustrated in FIG. 1, the process is begun at step 10. Relative inclusion area operation, step 40, then receives an inclusion area obtained in step 20 and the area of the diamond obtained in step 30 to determine a relative inclusion area. A parameterized relief value is obtained in step 50. A parameterized location (or position) value is obtained in step 60. A parameterized type value is obtained at step 70. These values—relative area, location, type, and relief—are then received in step 80 where they are used to find an appropriate lookup curve or table, and from which a numerical clarity grade is determined which corresponds to that particular combination of parameter values. The numerical clarity grade is then adjusted in step 100 according to the number of reflections and/or additional inclusions entered at step 90. This results in a final categorical (or parameterized) clarity grade being provided at step 110.

In an alternative embodiment, for steps 90 and 100, the number of inclusions data field may be replace by a reflections data field. Possible values for this data field may be none, moderate or obvious, for example. Other values may be used as appropriate. In step 90 for this alternative embodiment, such values for the reflections observed in the gemstone would be entered. Then in step 100, for this alternative embodiment, the numerical grade received from step 80 would be adjusted to account for the entered reflection values. For example, for a reflection value of "moderate" the numerical grade would be increased by an amount. For a reflection value of "obvious" the numerical grade would be increased by an even greater amount.

One of ordinary skill will appreciate that, while particular operations, forms or quantities are set forth in the blocks of FIG. 1, other similar or equivalent operations may be used as appropriate to implement the principles of the invention. For example, while a "lookup curve" is set forth in step 80, other mechanisms may be used such as look-up tables, data bases, or the like. Likewise, while a calculate operation is set forth in step 80, one of ordinary skill in the art will appreciate that other operations can provide the desired results, such as by way of look up tables, or programmed logic arrays, or the like. Similarly, while specific quantities, such as 5 and 0.5 are set forth, other values may be used within the spirit of the invention.

In order to convert parameters such as relative inclusion area, type of inclusion, relief, and location into a clarity grade, relationships between these factors and actual clarity grades given in a grading laboratory were established. To develop these relationships, data pertaining to thousands of inclusions were measured according to a multifold data collection program. However, because some combinations of parameters are extremely rare, measuring every known combination of inclusion parameters so as to fill-out a complete clarity grid is impractical. Efforts were thus initially focused on the most common parameter combinations, wherein research was confined to measuring single grade-setting inclusions in round brilliant cut diamonds. In the course of the study some of the initial data field categories for each of the inclusion parameters, such as the inclusion type parameter, the number of inclusions parameter, and the relief parameter, were combined to increase the amount of data in each data field category and thus provide more robust relationships. It is noted that for this study, the face-up position was the main observation direction for visual clarity grading of all clarity grades from VVS2 down. Therefore, in this study the face-up position was adopted as the standard observation direction for data collection and for taking digital images. Other observation directions, however, such as those arrived at by tilting may also be considered.

Figure 2A:
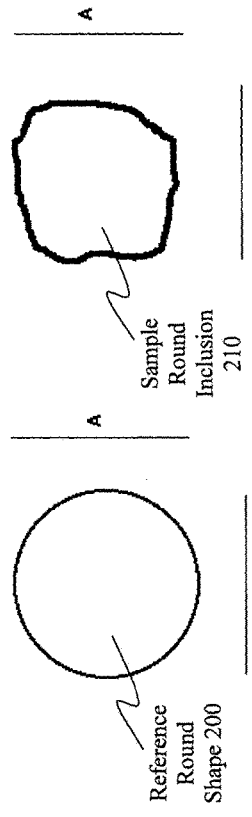
FIG. 2A is an exemplary guide for evaluating the dimensions of a round clarity characteristic.
Figure 2B:
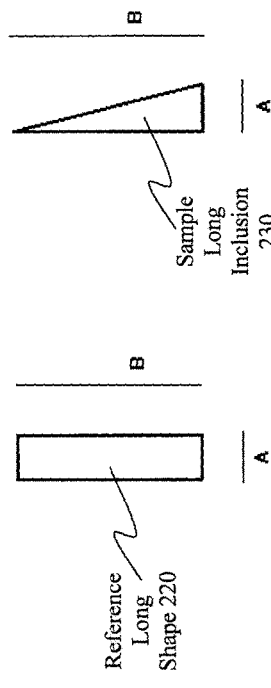
FIG. 2B is an exemplary guide for evaluating the dimensions of a long clarity characteristic.
Figure 2C:
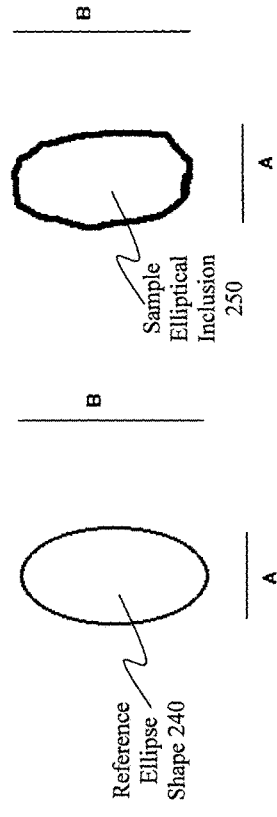
FIG. 2C is an exemplary guide for evaluating the dimensions of an elliptical clarity characteristic.

A brief summary of an exemplary data collection methodology for assembling clarity grading data according to an embodiment of the invention will now be discussed. First, a detailed uniform set of data collection guidelines and examples were produced for use by a data gathering grading staff, so as to provide uniformity and consistency in the gathered data. In FIGS. 2A-2C, an exemplary guide for evaluating the dimensions of a clarity characteristic is illustrated. FIG. 2A, for example, may be used by a grader to determine the "size" and "length" parameters of a "round" or "about round" characteristic. FIG. 2A provides dimensions for both a reference round shape 200 and a sample round inclusion 210. As can be seen in these diagrams, a "round" shape characteristic has size and length parameters that are approximately the same. This is indicated by the same letter, "A", appearing in both the x and y dimensions. For such a "round" shape, the grader is instructed to enter "A" for its "size," and "A" for its "length," where A is the measured quantity.

Similarly, the guidelines for a "long" characteristic may include reference long shape 220 and sample long inclusion 230 as shown in FIG. 2B. A "long" shape characteristic, according to FIG. 2B, has a length dimension "B" which is longer (e.g. visibly greater) than the size "A" dimension. Preferably, the grader is instructed to note that the inclusion has a "long" shape characteristic if its length is at least four (4) times the size. The measured values for the size "A" and length "B" are entered. From FIG. 2B it can be appreciated that "long" shape characteristics include shapes which are rectangle-like as well as triangle-like.

Guidelines for an elliptically-shaped characteristic may also be provided, which may include reference ellipse shape 240 and sample elliptical inclusion 250 as shown in FIG. 2C. As can be seen from FIG. 2C, an "ellipse-shaped" clarity characteristic has a length "B" which is visibly greater than its size "A," and a generally curved or oval shape. The measured values for size "A" and length "B" are entered.

Figure 3A:
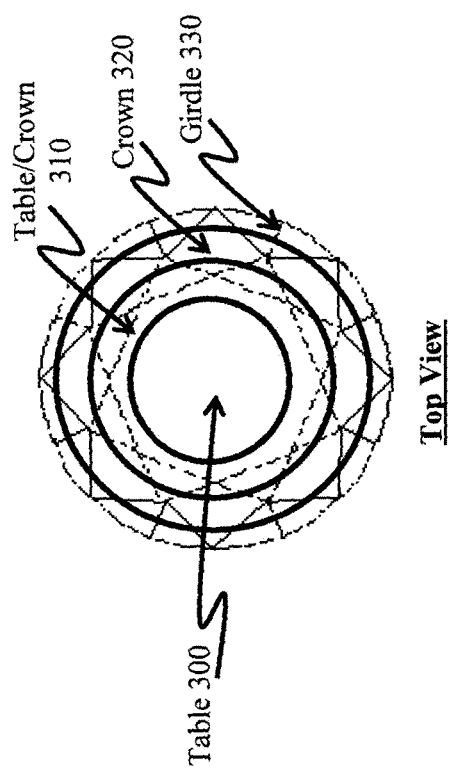
FIG. 3A is an exemplary guide for evaluating the location of an inclusion showing the top view of a gem.
Figure 3B:
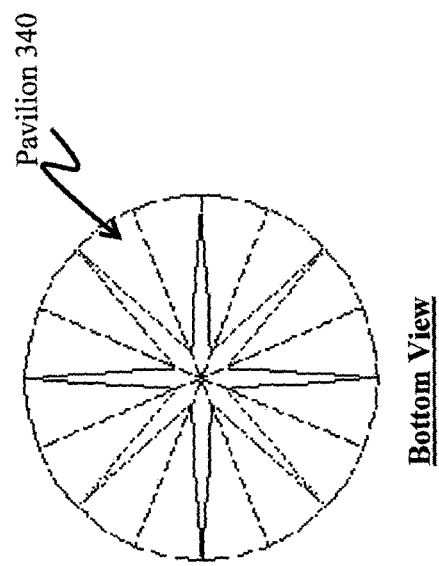
FIG. 3B is an exemplary guide for evaluating the location of an inclusion showing the bottom view of a gem.

The data collection guidelines may also be drafted so as to provide uniformity and a parameterization for the position parameter. FIGS. 3A-3B, for example, may be provided to graders so as to associate an inclusion with one of several possible position parameter designations. In this example, five possible locations are designated: Table 300; Table/Crown 310; Crown 320; Girdle 330; and Pavilion 340. A narrative may also be provided, which further specifies the boundaries of each location. For example, a position in Table 300 may require the inclusion's center of gravity to be within 80% of the table size. A position in Table/Crown 310 may require the inclusion's center of gravity to be within a region extending from the Table 300 boundary up to a boundary at about 50% of the star facets. A position in Crown 320 may require the inclusion's center of gravity to be within a region extending from the Table/Crown 310 boundary up to a boundary at about ⅓ of the upper girdle half. A position in Girdle 330 may require the inclusion's center of gravity to be within Girdle 330. A position in Pavilion 340 may require the inclusion's center of gravity to be anywhere in Pavilion 340.

It should be further noted that the data collection guidelines may also provide parameter guidance as to any of several more parameters, as well. Relief parameters, for example, may be quantified or parameterized. For example, instead of verbal relief assessments "very high relief," "high relief," "medium relief," "low relief," and "very low relief," numerical values 1-5, respectively, may be used, along with a designation of whether the relief has a white or black characteristic, as set forth in Table 1, for example:

TABLE 1

| Verbal Designation | Initial Parameterized "Relief" Categories | Alternate Parameterized "Relief" Categories |
|---|---|---|
| very high relief | RW1 or RB1 | RW1 or RB1 [High] |
| high relief | RW2 or RB2 | |
| medium relief | RW3 or RB3 | RW2 or RB2 [Medium] |
| low relief | RW4 or RB4 | RW3 or RB3 [Low] |
| very low relief | RW5 or RB5 | |

It is to be noted that while five relief categories are identified above, a fewer number of categories was ultimately adopted for use. Specifically, the relief parameter was consolidated from initially five categories into only three (i.e., High, Medium and Low or RW1, RW2 and RW3), with relief categories 1 and 2 being merged to correspond to a "High" relief category, and relief categories 4 and 5 being merged to correspond to a Low relief category. These alternate relief categories are noted in the third column of Table 1.

The "number of inclusions" parameter may also be streamlined or parameterized. For example, the numerical value 1 may be assigned if there is only one image; a value of 2 may be assigned if there are two images; a value of 3 may be assigned if there are 3-4 images; a value of 5 may be assigned if there are 5-7 images, and a value of 8 may be assigned if there are 8-10 images.

These foregoing guidelines are then used in a exemplary data collection methodology for assembling clarity grading data to gather inclusion characteristic data for each diamond in the collection of diamonds in the data base. A data collection worksheet, such as the worksheet provided in FIG. 4, may be used for initially recording the data. As can be seen from FIG. 4, data for up to three inclusions can be accommodated by the worksheet. The fields entitled Diameter or Weight, Length, Shape, Clarity Grade Diamond (and High, Medium, and Low) refer to the gem as a whole and the classifications assigned by the grading laboratory. The table, then provides a number of fields including fields for the magnification used; the inclusion "size" and "length" and whether it is "long"; clarity grade and three possible positions within the assigned clarity grade (High, Medium and Low); whether the inclusion is internal or surface-reaching; "position"; "Number"; "Type"; and "Relief" (Black or White).

A microscope equipped with a measuring graticule may be used to measure the length and width of the inclusion for the inclusion size parameter. These measurements are then noted on the worksheet in terms of "microns" or a number of "graticule scales". The "graticule scale" quantity can be converted to microns (or other dimensional units) as a function of the microscope's objective magnification or magnification factor. For example, a 1× magnification may result in one graticule scale equaling 100 microns; a 2× magnification may result in one graticule scale equaling 50 microns; 2.5× magnification may result in one graticule scale equaling 40 microns; and a 4× magnification may result in one graticule scale equaling 25 microns. Here, explicit instructions/guidance may be provided to the grader via the data collection guidelines to make note of such information.

For this particular example, it should be appreciated that the data collection methodology included a preliminary trial part, a trial evaluation part, and then a full program for collecting daily measurements and other data in multiple labs. In practice, the data collection was only done after the final clarity grade assigned by the lab was known for each diamond. The diamond was then examined by one of the appointed grading staff who made note of all the relevant clarity grading details and inclusion parameters on the worksheet. A digital image of each stone was acquired as a permanent visual reference and for working with a parallel computerized data processing system provided by the previously referenced Clarity Measurement Application.

Next, tools described in the Clarity Measurement Application were used to verify the data on the worksheets by cross checking them with details that can be seen on acquired images. To this end, the graticule scales may, for example, be recalculated in accordance with the microscope magnification factor to convert the inclusion Length and Width measurements into microns.

In the last step, the manually acquired data collection details from the worksheets were entered into a database, which allowed the data to be systematically queried at a later time. Where applicable, the abbreviations from the data collection guidelines were transformed into common descriptions used to construct the database.

Once data has been collected, relational database tools can then be used to ascertain mathematical relationships, by which a clarity grade may be predicted for particular parameter combinations. For example, a data base may be created using the Access Database product by Microsoft Corporation of Redmond, Wash. The data base consists of three relational tables (i.e., Table Inclusion 1, Table Inclusion 2 and Table Inclusion 3). Preferably, for each diamond studied, information from up to three grade-setting inclusions can be entered via the database's object electronic forms. The three tables (Tables Inclusion 1, 2 and 3) are preferably designed to contain all the necessary inclusion parameters needed for the theoretical clarity analysis including the measurements of each of the diamonds being studied and the details for up to three grade setting inclusions.

Figure 5:
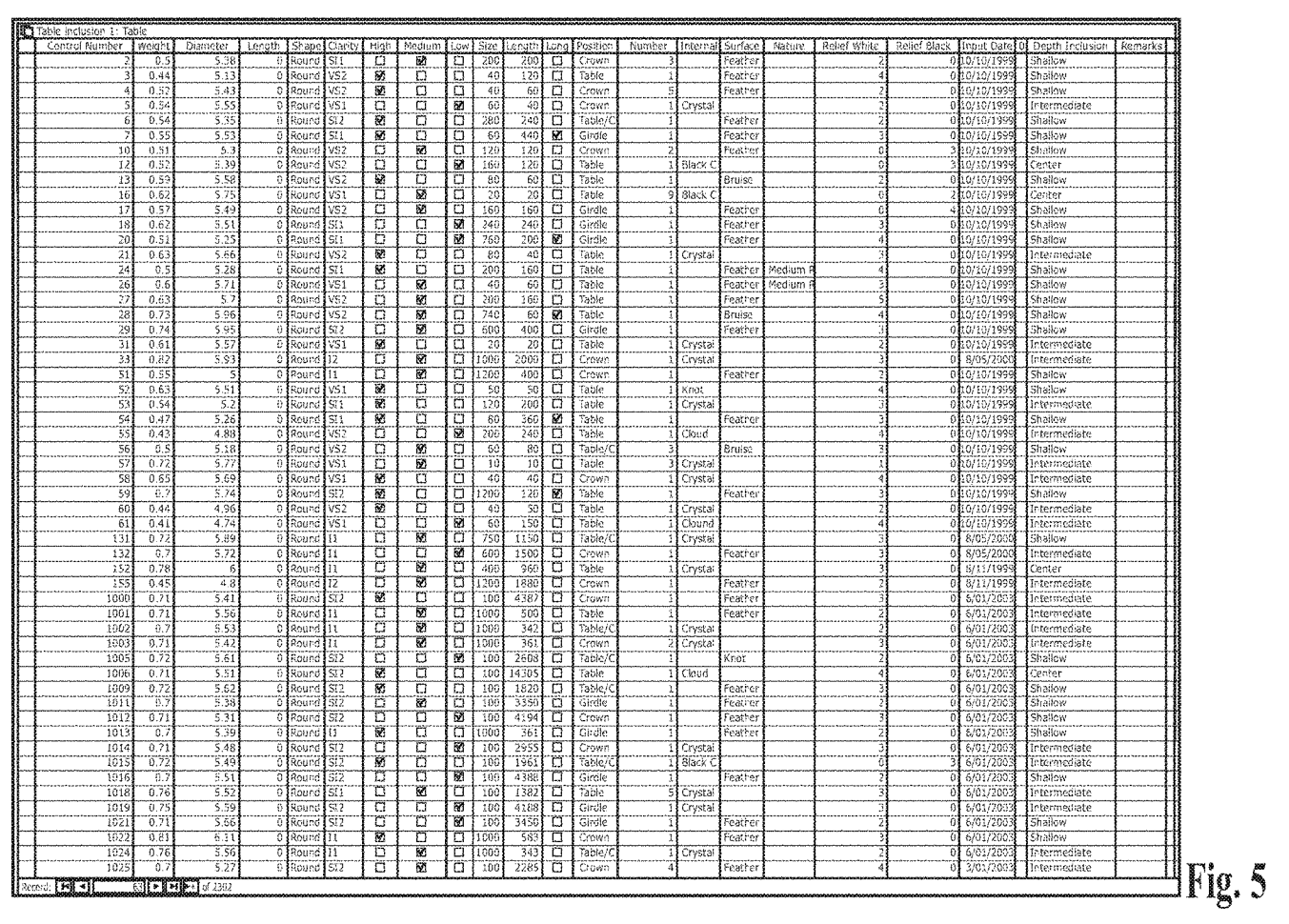

An exemplary Table Inclusion page, according to an embodiment of the invention, is provided in FIG. 5. For example, in the Table of FIG. 5, the diamond having control number 59 had a weight of 0.7 cts, a diameter of 5.74 mm, and a "Round" shape. A clarity grade of SI2 had been assigned to the diamond. The inclusion that was examined was judged to have a "Relief White 3" relief of size 1200 and length 120, and to be "long." The inclusion was located in the "Table" position, and was a single inclusion. The type of the inclusion was determined to be a "feather." In the table, the "High", "Medium" and "Low" fields are selected during the grading process in the laboratory, to indicate where the diamond is positioned in the range associated with the assigned clarity grade. Thus, for the example being discussed, diamond control number 59 was judged to be positioned at the high side of the SI2 clarity grade range.

In the Access database program, each specific data field in a database object table is specifically defined as numeric, as text, etc., as appropriate for the type of data (measured, verbally described or calculated) for each data field. The control number is set as the primary key to link the tables in the database structure. For this particular embodiment, a number of queries were designed to sort for inclusions with a type of "crystal" and "feather," in addition to calculating the relative inclusion area (inclusion area to diamond area) for each inclusion.

Figure 6:
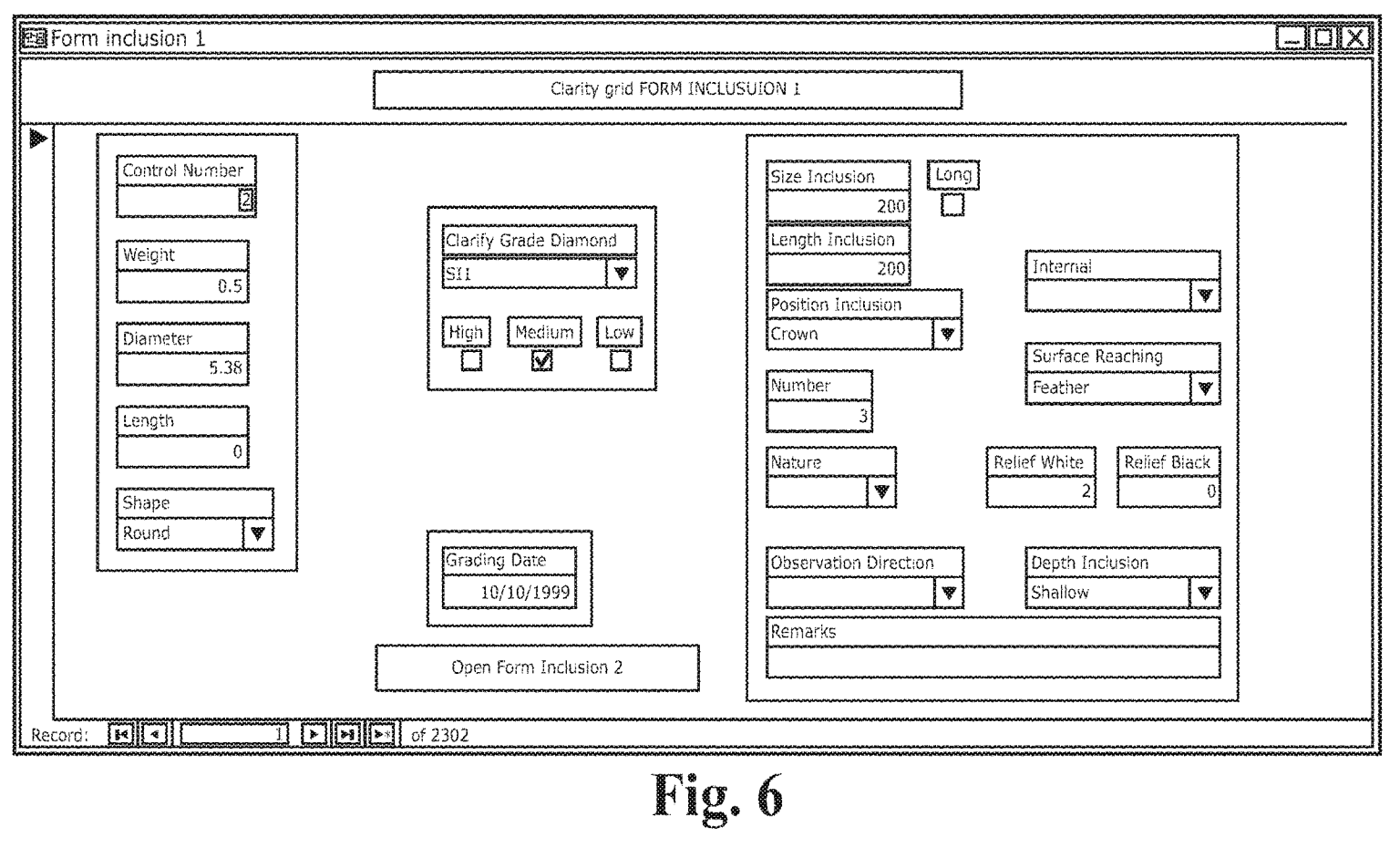

In a preferred embodiment, inclusion characteristics are entered through input forms, which are linked to the tables. An example of such an input form, provided in FIG. 6, allows for easy toggling from one data field to another for fast data input. As can be seen from FIG. 6, data entry fields are provided for each of the fields found in the worksheet of FIG. 4. Drop down menus are provided for parameterized characteristics, such as for position, number, type, and others. For this particular embodiment, there were three input forms for up to three grade setting inclusions linked to the related tables.

An advantage of using a relational database is that subsets of the data can be formed via queries of existing or additional data fields. An example of a queried page, according to an embodiment of the invention, is provided in FIG. 7. For this particular embodiment, an initial query was made which required added data fields for the metric calculation of the inclusion area (in square mm; e.g., based on the equation of an ellipse, which requires inclusion "Length" and "Size" measurements), and the diamond area (in square mm; e.g., based on the diameter of the stone). For subsequent queries, a data field may be added which calculates the relative inclusion area (expressed as a percentage) based on the two previous calculations. For queries on crystals and feathers, still more data fields may be added which link the Tables (i.e., Table Inclusion 1, 2 and 3) allowing sorting of the data from the Tables by the relative inclusion area. In connection with the data collection and validation process, databases from different grading laboratories should preferably initially be kept separate until a comparison between the contents of the databases (e.g. to verify consistent data gathering and evaluation techniques and criteria) indicates that the data can be safely merged into a single common database.

In order to better appreciate particular aspects of the present invention, results from an actual test case are now provided. For this case, an initial test sample selection of 250 stones was used to evaluate data collection guidelines and to look for preliminary relationships between the inclusion parameters and the assigned clarity grade. From this evaluation, predictions were made about the amount of data that would be needed to provide statistically sound relationships.

Testing the 250 sample stones was carried out in two grading laboratories, which initially included two separate databases that were updated as new data became available.

In order to ascertain whether the two databases could be merged, a comparison between the contents of each database was made by running a number of similar queries on both databases. This comparison showed no significant difference between the two databases when sorting by relative inclusion area and comparing size averages with corresponding clarity grades, with other inclusion parameters held constant. Therefore, because records for the two databases were sufficiently similar and compatible, both databases were combined into a single database. As a result, the amount of data was increased, which provided more robust mathematical relationships between the individual parameters and the clarity grade to be calculated.

Mapping the distribution of the data across all the parameters and data fields provided an assessment of where incomplete and missing data fields still existed. The regular mapping allowed for adjusting the data collection program to fill in the gaps or combinations of parameters with sparse data. The mapping also provided a prediction of how many records were still needed to provide minimal requirements for each combination of parameters to establish statistically sound relationships. Exemplary mapping distributions are provided in FIGS. 8A-8B.

In FIG. 8A, for example, a mapping distribution of inclusions having a "crystal" type across all parameters and data fields is illustrated. As illustrated, entry 810 indicates that five records exist for a diamond having a VS2 clarity grade, with the crystal inclusion located in the Table position; and has a parameterized white relief parameter of 1. Gap 820, however, indicates that no records had been entered for a diamond having a VS2 clarity grade, with a crystal inclusion located in the Table/Crown position; and a parameterized white relief parameter of 1.

Similarly, FIG. 8B provides a mapping distribution of feathers across all parameters and data fields. As illustrated, entry 830 indicates that one record exists for a diamond having a SI1 clarity grade, wherein the diamond includes a feather inclusion located in the Table position; and has a parameterized white relief parameter of 1. Gap 840, meanwhile, indicates that no records have been entered for a diamond having a SI2 clarity grade, wherein the diamond includes a feather inclusion located in the Table position; and has a parameterized white relief parameter of 1.

For this particular test case, it should be noted that the dataset was enhanced by combining the manually collected data with data collected using the techniques described in the earlier referenced Clarity Measurement Application, by the inclusion's area size, position, and relief can be measured in a semi-automated way. It should be noted that the techniques described in the Clarity Measurement Application automatically calculate the inclusion area and relative inclusion area once the digital images have been calibrated. To be compatible with the existing database structure (database objects and data fields), these area calculations were converted to inclusion Length and Size parameter data fields in order to match the existing database. This was possible by defining a fixed inclusion Length value for each clarity grade to be used in a formula to back calculate the inclusion Size value.

As an example of how this back calculation is done, consider a diamond having the following parameter values from an existing data base and based upon manual inclusion measurements:

Diameter=6.48 mm
Weight=1.02 cts
Shape=RBC

In the original manual inclusion measurements, the width was measured as 3 graticule scales at 2× magnification. This corresponds to 150 μm, based upon 50 μm per graticule unit at 2× magnification.

The length was measured as 17 graticule scales at 2× magnification. This corresponds to 850 μm, based upon 50 μm per graticule unit at 2× magnification.

The original determination of inclusion area in microns was based upon the relationship:

Area_inclusion: (([Table inclusion 1]·[Size Inclusion]
*[Table inclusion 1]·[Length Inclusion])*(314/
400))/1000000

In the above relationship, [Table inclusion 1]·[Size Inclusion] corresponds to the value of the "size" field for inclusion 1 of subject gem in the table for the, and [Table inclusion 1]·[Length Inclusion] corresponds to the value of the "length" field for inclusion 1 of the subject gem in the table.

Recall from the description, provided earlier, of the data collection methodology used to assemble the clarity grading data analyzed in connection the invention, that an equation for an ellipse may often be used to approximate inclusion area using the above "size" and "length" measurements:

$$Area_{inclusion} \approx Area_{ellipse} = \pi \times (size/2) \times (length/2)$$

The Area_inclusion relationship above, thus implements an ellipse area calculation in which, in the numerator π is approximated as 3.14 and multiplied by 100 to provide an integer form. In the denominator the value of 400 is obtained from the divide by 2 factors for the "size" and "length", and includes a multiply by 100 to account for the integer conversion of the approximation of π. The value of 1,000,000 in the denominator of the Area_inclusion relationship is used to convert square microns into square millimeters (mm).

Applied to the above quantities, the result is:
inclusion area size=0.100 square mm Then the diameter of the diamond is used to calculate the diameter face up area of the diamond using an approximation for the area of a circle: $3.14 \times (d/2)^2$, where d=diameter of the diamond. The relative inclusion area is then calculated using the data base fields of [Query400crystalAREAcal]·[Area_inclusion] and [Query400crystalAREAcal]·[Area_diamond], according to the relationship:

Area_relative: ([Query400crystalAREAcal]·[Area_inclusion]/[Query400crystalAREAcal]·[Area_diamond])×100 where a multiply by 100 is used to transform the result into percentage form.

Applied to the above quantities, the result is:
relative area inclusion=0.304%

This result is multiplied by 1000 to transform it into integer form for use in plotting and deriving Relief versus Relative Area relationships.

For the above diamond, the clarity grade assigned by the lab was "SI2".

As discussed above, as part of the data collection process in order to enhance the dataset used in developing the clarity grading methodologies of the present invention, diamonds were remeasured using the pixilated image analysis techniques to provide inclusion measurements. These measurements were then converted to inclusion Length and Size parameter data fields in order to be in a consistent format with the existing database, and so as to make it possible to use the existing data base data fields. An example of such conversion will be now described:

For the same diamond described above, the inclusion area measured using pixilated image analysis was:
area inclusion=0.115

From the pixilated image based measured area inclusion, and the diamond area calculated by the measured diamond diameter, a relative inclusion area was calculated to be:
relative area inclusion=0.348

The pixilated image based area inclusion was then converted into Size and Length values by using a fixed value for the Size, depending on the clarity grade assigned to the diamond having that inclusion. Preferably, the particular magnitudes are chosen in order to avoid overly large values for Length. Preferably, the fixed values for Size may be 10 for a VS clarity grade, 100 for a SI clarity grade, and 1000 for a I clarity grade. Using those fixed Size values yields Conversion Values, such as 127400, 12740, or 1274 (for VS, SI, or I, clarity grades, respectively) which when multiplied with the area inclusion value, results in a reconverted Length value. The Conversion Values can be derived from the formula for calculating Length, which is:

Length (in μm)=(Area$_{inclusion}$ (in square mm from pixilated image analysis measurement)×1,000,000×(400/314))/$S$ (fixed, in μm)

Or:

Length (in μm)=Area$_{inclusion}$(square mm)×1,274,000/$S$(μm)

Therefore,

Conversion Value=1,274,000/$S$(μm)

The following table sets forth for each clarity grade, the preferred fixed Size value, and resulting the Conversion Value.

| Assigned Clarity Grade | Fixed Size value | Conversion value |
|---|---|---|
| VS | 10 | 127400 |
| SI | 100 | 12740 |
| I | 1000 | 1274 |

For the diamond of the example, the clarity grade previously assigned was SI2. This corresponds to a fixed value for the Size=100, and a Conversion Value of 12740. Thus, Length = 0.115 × 12740

= 1465 μm.

When this is entered into the data base the relative area inclusion=0.348(%) which is the same as calculated by the pixilated image analysis described herein.

It is noted that the earlier manual measurements made for the diamond of this example yielded a relative area inclusion of 304 (%×1000), while the pixilated image analysis yielded 348 (%×1000). For this example as in most examples, the margin of error (304 versus 348) between the manual measurement and the application measurement is considered to be very acceptable.

It should be further noted that, the efficacy of the data collection approach using techniques described in the Clarity Measurement Application depends on the quality of the digital images produced. Namely, high resolution digital images are required and must be taken under lighting conditions suitable for illuminating inclusions without too many reflections hindering the identification of the inclusions. An apparatus for achieving such high quality images is provided in application is provided in U.S. patent application Ser. No. 12/287,188, entitled "Reflected Dark Field Method And Apparatus," filed even date herewith, and incorporated herein by reference in its entirety.

Once sufficient data was collected using techniques described in the Clarity Measurement Application, a comparison study between the first and second data collection methodologies was made to determine the feasibility of combining both sets of data for future analysis of the complete data record set. To assure full compatibility of all the data, the original manually measured records were also digitized using the techniques described in the Clarity Measurement Application with the results converted to match the form of second, computerized data collection records. More specifically, the same diamonds for which manually measured records already existed, were processed again using the techniques described in the Clarity Measurement Application, and the obtained parameter values were converted to be compatible with the data fields in the original measurement records. As such, this conversion insured that both data sets could be legitimately merged into a single database for analysis.

Two independent methodologies were developed to analyze the collected data in an effort to empirically model the relationships between the inclusion or clarity parameters and the clarity grade. The first methodology was a "most reasonable fit" method based on a reasonable fit average for a selection of records. This first method makes use of selecting only the most robust records from the database. For this method, records that returned a questionable final result, or had corrupt data fields, were excluded from the selection. Moreover, a subjective criteria was used which set boundaries for each parameter based on a visual assessment of the average and range of values in each adjacent category. Records were then excluded if they did not fall within the set boundaries, which effectively removed outliers from consideration in the analysis. Records with overlapping final results were also re-examined and excluded from the selection when the overlap could not be logically justified. For the remaining selection of records, the statistical operators mean, minimum, and maximum of the inclusion size parameter were plotted against each of the other inclusion parameters.

The second method was a "standard statistical" method, which applied statistics that utilized all the records in the database, including outliers. The use of the second method, although scientifically more sound than the first, was more vulnerable to the effects of corrupted data. The second method was particularly vulnerable for parameter combinations having a small sample size, since the average of only a few records is relatively more susceptible to erroneous or misleading outliers than the average of a larger set of records. For the "standard statistical" method, the inclusion size parameter was plotted against each of the other inclusion parameters using the same statistical operators that were applied in the "most reasonable fit" method, but also including median. The entire dataset including outliers was used. A comparison of the results of the two methods was then made to see if a more standard statistical approach (the "standard statistical" method) provided better or worse predictive value than the "most reasonable fit" approach. Although both methods worked adequately, the "most reasonable fit" method was selected as the preferred method.

In support of the analysis of both methods, diamond images were re-examined by clarity graders when related data records differed in an inexplicable manner from the general trend of other observations. In these cases, the data entries were also checked again. Although this selective procedure introduced a degree of bias to the analysis, it was believed that the benefits of addressing obvious mistakes outweighed the negative consequences of potential bias. It should also be noted that, because both analysis methods indicated that the inclusion parameters for crystals and feathers influenced the clarity grade differently, crystals and feathers were treated and analyzed separately.

Analytical modeling of the relationships allowed a weight to be given to inclusion parameters for the size, the position and the relief for one grade setting inclusion. As mentioned previously, retaining as much as five relief categories was not desirable as the subtle distinctions were not reproducible and having five categories also left too many gaps in the clarity grid. Combining relief factors boosted the numbers of diamonds in each category significantly enough to fill in most of the gaps.

Despite this effort to consolidate data, however, some clarity grid gaps still existed since some types of clarity characteristics (e.g., knots and bruises) are rare and examples are difficult to obtain in sufficient numbers. Because other types of inclusions such as feathers and crystals are commonplace, this test case concentrated on those feather and crystal inclusions to address most of the diamonds in the sample set. It was also found that common clarity characteristics can serve as proxies for some of the rarer types. For example, a proxy for "knots" may be "crystal;" a proxy for "bruises" may be "crystal," a proxy for "dense clouds" may be "crystal."

Figure 9:
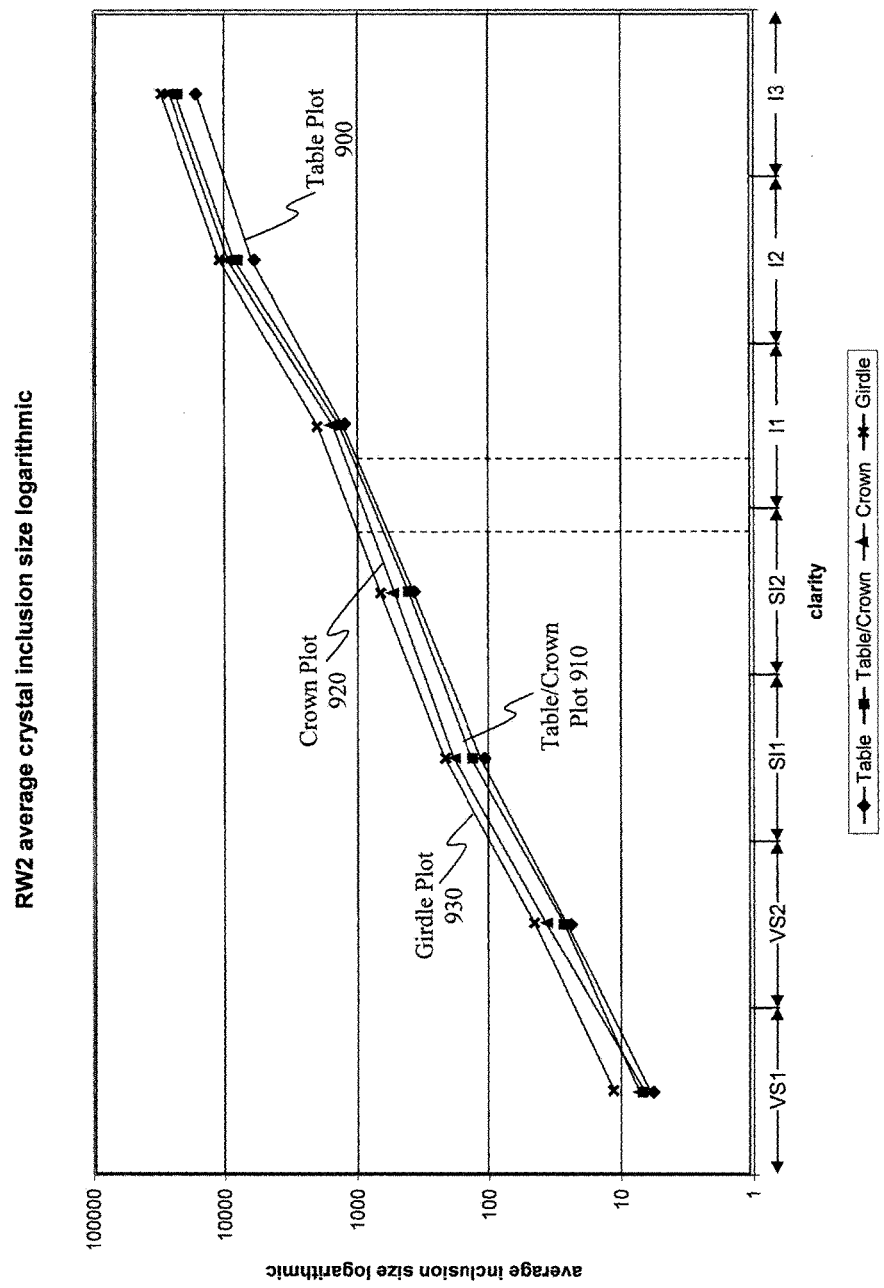
FIG. 9 is a set of log-normal graphs illustrating the relationship between relative inclusion size and clarity at particular locations on a gem which was determined in accordance with an embodiment of the invention.

As a result of the foregoing efforts, for inclusions having a "type" of feathers or crystals, relationships between relative inclusion size and clarity, for each combination of variables, were found to be logarithmic. An exemplary illustration of such a logarithmic relationship is shown in FIG. 9, wherein log-normal graphs representative for crystals having "medium" relief (RW2) are provided. As illustrated, each of the lines represents one of the parameterized inclusion locations—Table, Table/Crown, Crown, or Girdle—where the grade-setting inclusions are located. It can be seen that each line is nearly linear on a logarithmic normal plot, implying a straightforward exponential relationship. For example, Table Plot 900 represents this relationship for inclusions located in the Table region; Table/Crown Plot 910 represents this relationship for inclusions located in the Table/Crown region; Crown Plot 920 represents this relationship for inclusions located in the Crown region; and Girdle Plot 930 represents this relationship for inclusions located in the Girdle region. The vertical axis in FIG. 9 represents the "average inclusion size logarithmic," which relates to the logarithm of the relative size of an inclusion, where the plotted relative size values has been multiplied by a factor of 1000 to eliminate the decimal point for convenience in creating these plots. The horizontal axis in FIG. 9 is divided up into seven (7) ranges representing parameterized clarity grades: VS1, VS2, SI1, SI2, I1, I2 and I3. The points plotted in FIG. 9 represent the average relative size (logarithmic) for inclusions in diamonds having the same parameterized clarity grade, and where the inclusions have a "type" of "crystal," and a relief of "RW2," in each of the different possible "locations." For example, in FIG. 9 it can be seen that the average size (logarithmic) of inclusions in diamonds assigned a SI1 clarity grade, where the inclusions were located in the Girdle region, was approximately 250, while for diamonds with inclusions located in the Table region the average size (logarithmic) of the inclusions was slightly greater than 100.

Relationships between position, size, and clarity grade, where relief and type are held constant (here, medium relief and crystal type), can thus be readily ascertained through FIG. 9. For example, FIG. 9 shows that more relative inclusion area is needed at the girdle position than the table position to yield the same clarity grade. As a further example, from FIG. 9 it can be seen that for a diamond having an inclusion with a type of "crystal", a relief of "RW2", and a relative size (logarithmic) of 1000, if that inclusion is positioned in the Girdle region (see Girdle Plot 910), the clarity grade would be predicted to be "SI2." However, if that same inclusion were positioned in the table region (see Table Plot 900), the predicted clarity grade would be "I1."

Figure 10A:
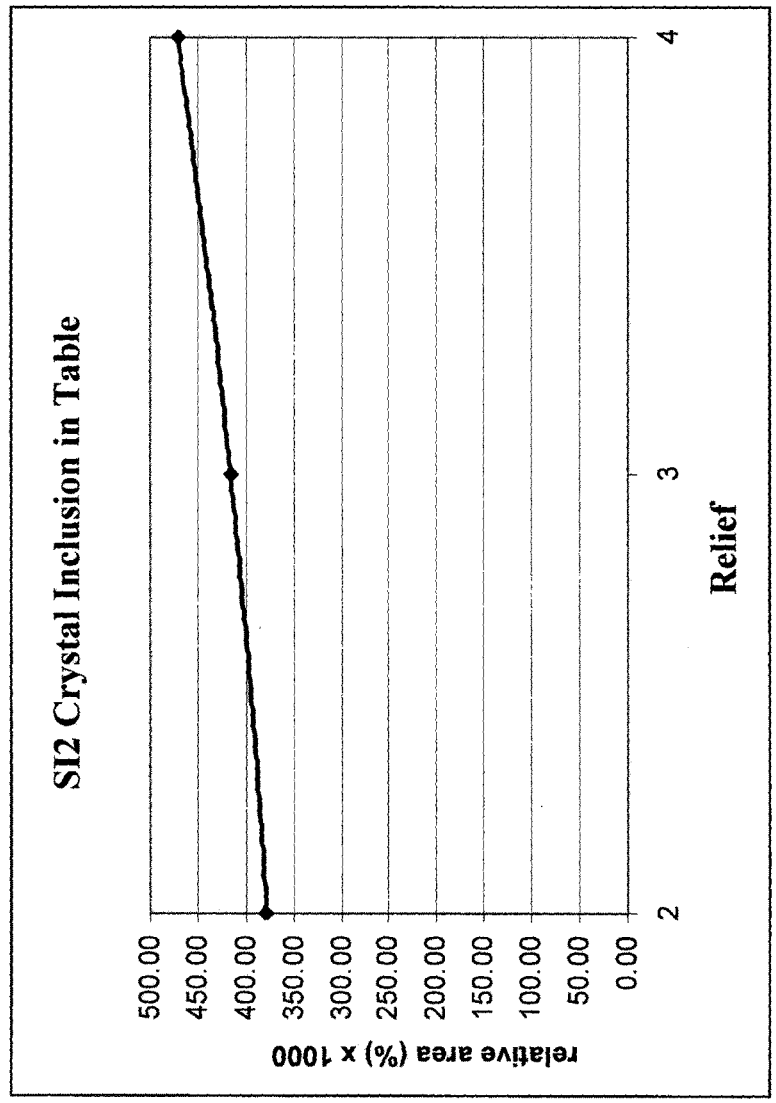
FIG. 10A is a graph illustrating the relationship between relief and relative inclusion size for an SI2 gem having a crystal inclusion in the table which was determined in accordance with an embodiment of the invention.

Relationships between other characteristics, may also be ascertained. In FIG. 10A, for example, the relationship between relief and relative area (normal, multiplied by scaling factor of 1000) for an SI2 grade gem is shown, for inclusions having a type of "crystal" and which are located in the Table region. As illustrated, more relative inclusion area is needed for a low relief (R4) inclusion to equal the same SI2 grade as a high relief (R2) inclusion.

Regression analysis (either via the "most reasonable fit" method or the "standard statistical" method) was then used to find the "best fitting equation" for plots of various clarity grades corresponding to particular parameter combinations found in the dataset. These relationships were then used as the basis for a model which predicts the clarity grade when the inclusion size and all the other combination of parameters are known. These predictive models may also be embodied as look-up tables in a computer application.

Figure 11A:
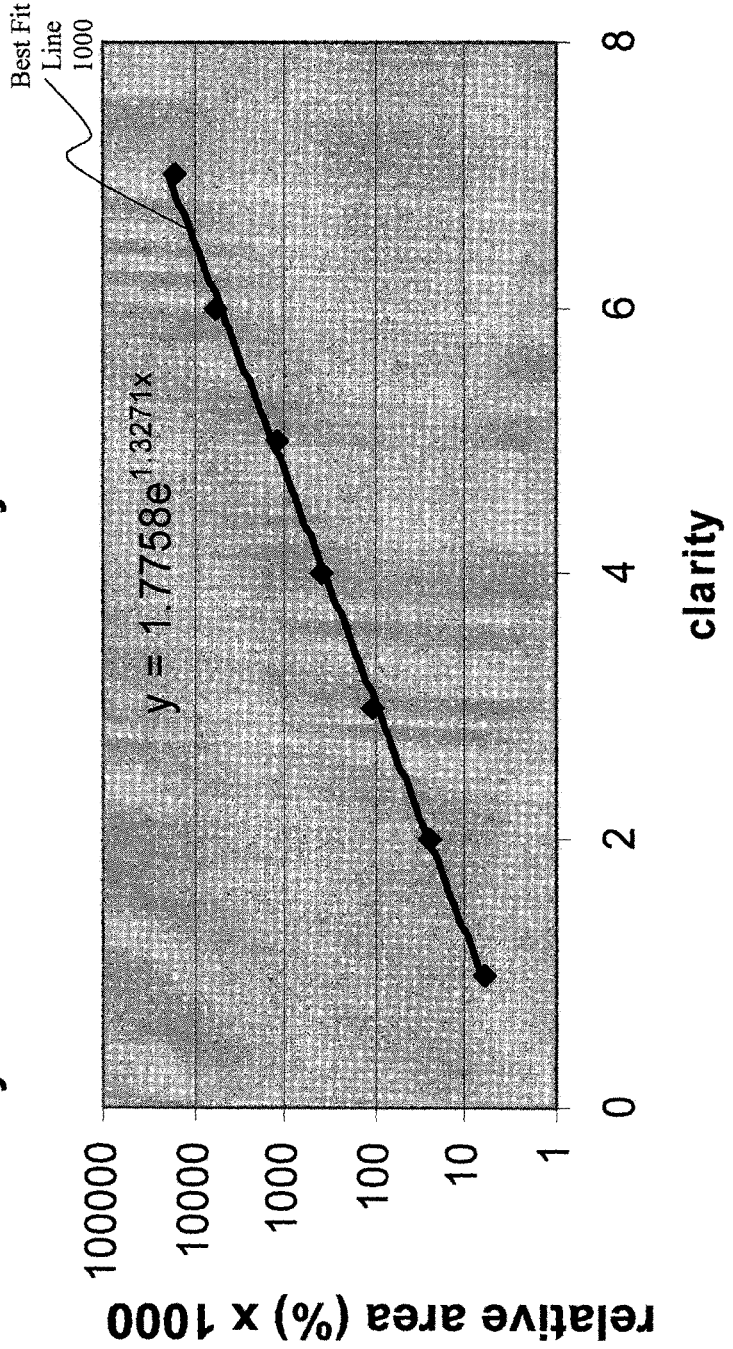
FIG. 11A is a log-normal graph illustrating the relationship between size and clarity which shows the best fit line for RW2 crystals in the table which was determined in accordance with an embodiment of the invention.

An exemplary log-normal plot illustrating such a best-fit equation is provided in FIG. 11A. For this particular illustration, it should be appreciated that "RW2" refers to the relief (R) category of white crystal inclusions (W), and a relief factor of 2 (recalling that the original five relief categories were combined into three categories). The numbers on the x-axis refer to clarity grades where grade 1=VVS2, grade 2=VS1, 3=VS2, 4=SI1, 5=SI2, 6=I1, 7=I2, and 8=I3. The formula shown on the plot is the equation of the line 1000 that is drawn to best fit the average of the observations of white "crystal" inclusions in the Table region having relief factor 2 (RW2). For this particular example, the best-fit equation was determined to be:

$$y=(1.7758e^{1.3271x}$$

Solving for "x" in the above equation, yields the relationship for a clarity grade value of:

$$x=(\ln(y/1.7758))/1.3271$$

Figure 11B:
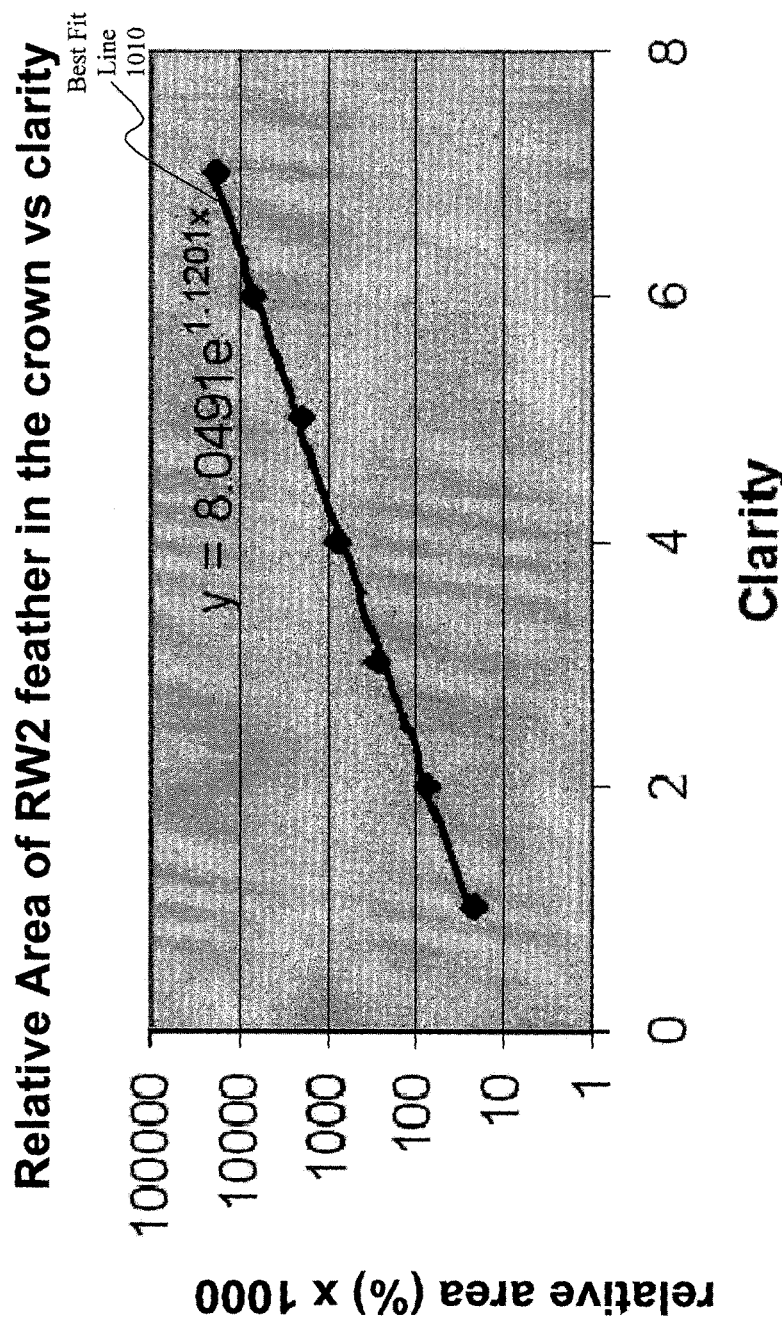
FIG. 11B is a log-normal graph illustrating the relationship between size and clarity which shows the best fit line for RW2 feathers in the crown which was determined in accordance with an embodiment of the invention.

Another exemplary log-normal plot illustrating such a best-fit equation is provided in FIG. 11B. For this particular illustration, it should be appreciated that "RW2" refers to the relief (R) category of white crystal inclusions (W), and a relief factor of 2. The formula shown on the plot is the equation of the line 1010 that is drawn to best fit the average of the observations of white "feather" inclusions in the Crown region having relief factor 2 (RW2). For this particular example, the best-fit equation was determined to be:

$$y=8.0491e^{1.1201x}$$

Solving for "x" in the above equation, yields the relationship for a clarity grade value of:

$$x=(\ln(y/8.0491))/1.1201$$

To evaluate performance, results from both the "most reasonable fit method" and the "standard statistical method" were compared with actual lab grade results once the application with the look up tables was built. A selection of records was made for a "test on crystals" and a "test on feathers". Only examples with solid grades were considered, not borderline cases. In evaluating the results mismatching results were particularly evaluated since these would directly contradict the algorithms that were used to produce the look up tables. Selections of borderline cases would have alternative explanations that have little to do with the analysis method. A sufficient number of matching results as detailed here suggests that the look up tables were indeed working properly.

In practice, the testing of the look up tables of the application proceeded as follows. After loading an image from one of two selected file folders (i.e., crystal or feather), an operator ran the different steps of the application until the application returned an actual laboratory clarity grade, as well as a sub-grade for each of the analysis methods. For testing purposes, operator interaction was allowed, wherein manual (but usually minor) changes to one of the parameters was occasionally necessary to derive reasonable results. Most of the time, it was found that these minor changes were associated with either the relief parameter or the inclusion size parameter, whereas changes to the position parameter were rare.

For the "test on crystals," a selection of 241 records had only 10 records that did not match the lab grade. In 8 of the 10 records that did not match, both analytical methods returned a grade different than the lab grade. The "strict agreement rate" percentage for the "test on crystals" selection was 88% based on the results of the best performing method operating on the parameter values as input without modification. A "practical" agreement rate of 96%, however, was achieved when an operator was permitted to override particular input parameters, such as relief, that the operator felt were unreasonable.

Meanwhile, for the "test on feathers," 35 of the 263 selected records did not match the lab grade. In 5 of the 35 records that did not match, a grade similar to that of the lab was returned by one of the methods. For the other 30 records, however, both methods returned a grade different than the lab. When comparing the grades from each of the two methods to the final grade assigned by the operator, the number of matches on a total of 263 selected records was 206 for the first method and 197 for the second method. Both the "most reasonable fit" and the "standard statistical" methods were found to provide satisfactory results, with the "most reasonable fit" method being considered slightly better and selected for further use, including use for the "test on crystals". The "strict agreement" rate percentage for the selection of feathers was 78% based on the results of the best performing method, whereas the manual override "practical" agreement rate percentage for this selection was 87%.

In summary, the above evaluation of the present invention's functionality yielded favorable results. The combined theoretical agreement rate for feathers and crystals was 83%, wherein operator interaction improved the agreement rate to 91%. It should also be noted that no records (either for crystals or feathers) for either analytical method ever differed from the lab grade by more than a grade. Also, except for the VVS2/VS1 clarity grade border for crystals, there was no easily definable difference between the two analyzing methods. As mentioned earlier, the "most reasonable fit" method was selected as the method for further use in the application.

In practice, the present invention thus provides a reasonably accurate clarity grade estimate based on particular gem/inclusion characteristics identified by a grader. Namely, a tool is provided in which gem/inclusion characteristics identified by a grader (both numeric and verbal) are parameterized and provided to a system that outputs a clarity grade based on the particular combination of parameterized values obtained. In order to better appreciate how the present invention might be applied, a specific example is provided below of obtaining the clarity grade of a round-cut diamond.

Referring back to FIG. 1, first, the grader may gather information regarding an inclusion's relative size for use in steps 20, 30 and 40. To this end, it should be appreciated that such information may be obtained in any of several ways, including manually or via the techniques set forth in the above referenced Clarity Measurement Application. Moreover, this information may include a verbal assessment of the relative size (e.g., "very small") which is converted to a corresponding numerical value, or an actual measurement taken either manually or via the techniques set forth in the Clarity Measurement Application. Inclusion relief characteristics are received and parameterized in step 50; position or location values are parameterized in step 60, and a type parameter is input in step 70.

Each of the parameterized values are then input to a system (e.g., a look-up table or computer program) that outputs an initial numerical grade estimate $G_{initial}$ as a function of the parameterized values, wherein the following equation may be used:

$$G_{initial} = f(P_{size}, P_{position}, P_{type}, P_{relief})$$

Namely, the above equation preferably represents a predetermined mathematical relationship between preliminary numerical grade estimates $G_{initial}$ and particular combinations of parameterized values $P_{size}$, $P_{position}$, $P_{type}$, and $P_{relief}$.

Next, in steps 90 and 100, a grader may account for additional inclusions/reflections in the diamond by lowering $G_{initial}$ by a predetermined constant $K_{additional}$, depending upon how influential additional inclusions are deemed to be. Where no additional inclusions/reflections are present, $G_{initial}$ is passed directly to step 110 for conversion in to a categorical clarity grade from among: IF, VVS1, VVS2, VS1, VS2, SI1, SI2, I1, I2 and I3, for example. If additional inclusions/reflections are present, $K_{additional}$ might be set at 0.5 such that the initial grade estimate $G_{initial}$ is increased by 0.5 if more than five additional inclusions are detected; a more moderate number of additional inclusions/reflections may increase the grade by 0.75; and a more severe number of additional inclusions/reflections may increase the grade by a full 1.0 grade. A final numerical grade $G_{final}$ may then be characterized by the following equation:

$$G_{final} = G_{initial} + K_{additional}$$

Once a final numerical grade is determined, the numerical grade is converted into an actual categorical grade according to a predetermined range of values. Namely, the final numerical grade may represent a parameterized clarity grade value that could then be converted to an actual clarity grade. For example, a particular range of values for $G_{final}$ could be assigned to a clarity grade of VS1 (e.g., where $X < G_{final} \leq Y$), whereas a different range of values might be assigned to a clarity grade of VS2 (e.g., where $Y < G_{final} \leq Z$). Similarly, ranges of $G_{final}$ would be specified for the other categorical (or parameterized) Clarity Grades: IF, VVS1, VVS2, SI1, SI2, I1, I2 and I3.

Figure 7:
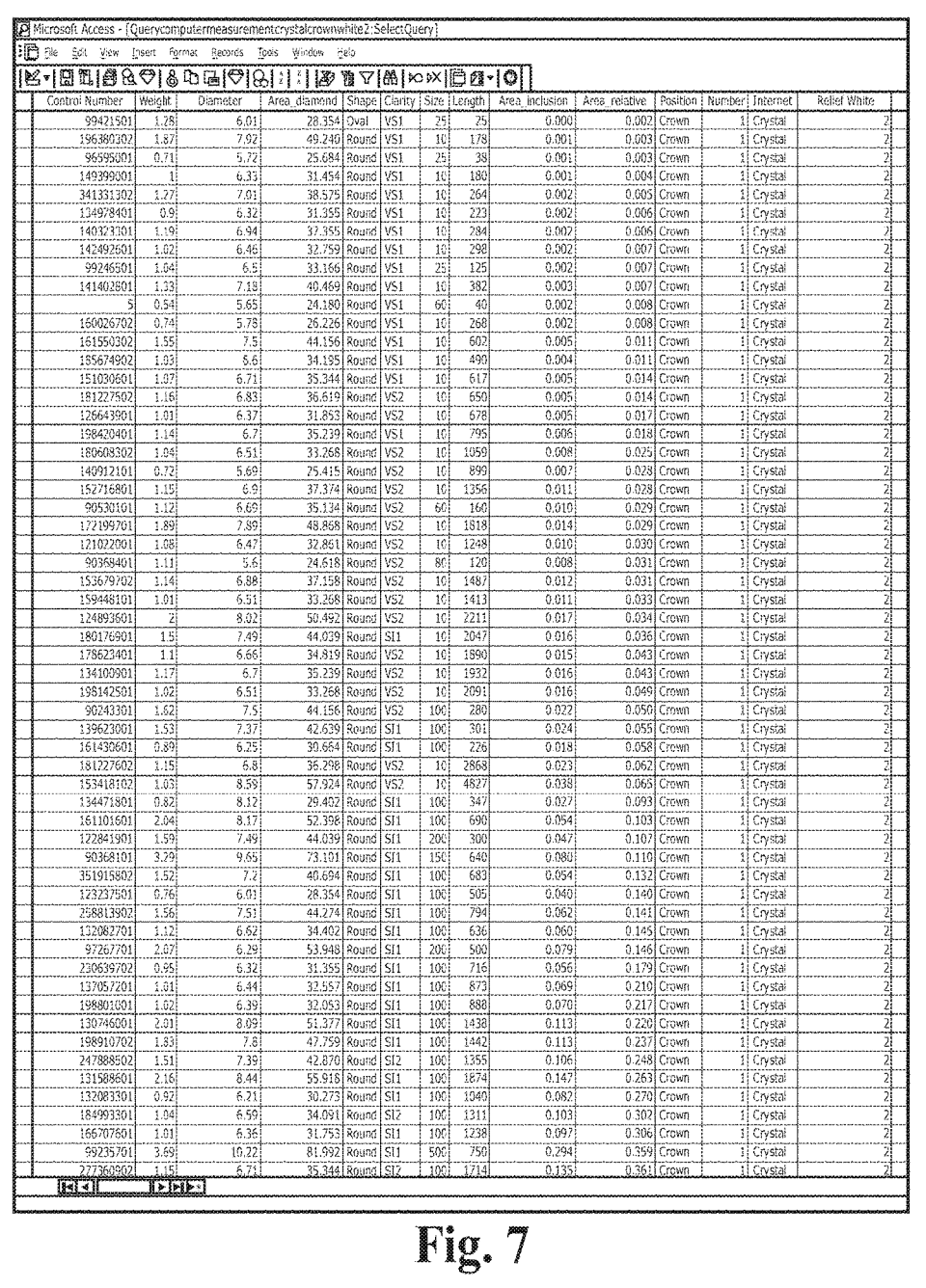
Figure 10B:
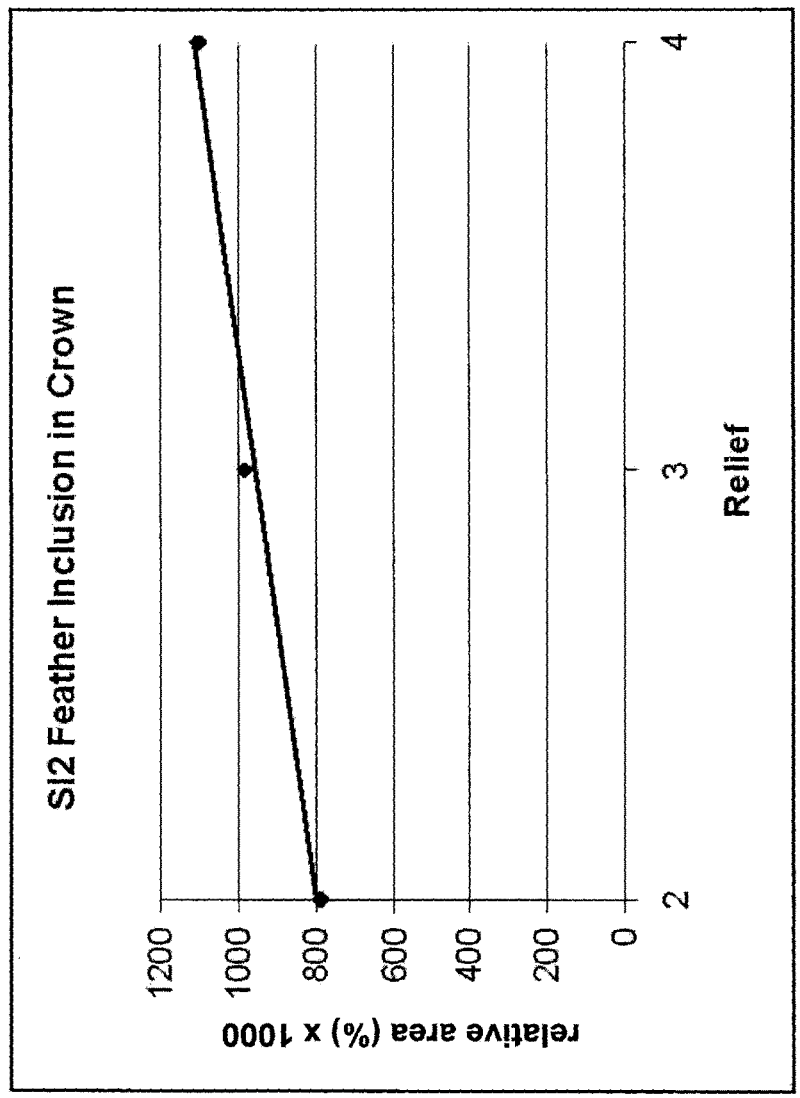
FIG. 10B is a graph illustrating the relationship between relief and relative inclusion size for an SI2 gem having a feather inclusion in the crown which was determined in accordance with an embodiment of the invention.

As a more specific example, assume that inclusion characteristic values were obtained for a diamond such as those listed for control number 140912101 in FIG. 7. Such values would indicate a single inclusion with area of 0.007 mm$^2$, a diamond area of 25.415 mm$^2$, a position in the Crown region, a "type" of "crystal", and pixel values for the inclusion that would be parameterized to a relief of Relief White 2 (RW2). The relative size of the inclusions would be determined to be 0.007/25.415=0.000275 or 0.028%. Applying a scaling factor, such as ×1000, used in FIGS. 9-11, a relative size value of 28 would be assigned to the inclusion, in step 40 of FIG. 1.

The various inclusion parameter values ($P_{size}$=28, $P_{position}$=Crown, $P_{relief}$=RW2, $P_{type}$=crystal, number=1) would then be used in steps 80 and 100, FIG. 1, to obtain a numerical clarity grade, $G_{initial}$, and then final numerical grade, $G_{final}$. In step 80, a look-up table or an equation (similar to those illustrated in FIGS. 11A and 11B) for RW2 crystals located in the crown, would be used to determine the corresponding $G_{initial}$ for $P_{size}$=28. Then, in step 100, it would be determined if an adjustment was needed in view of the number of inclusions found in the stone. The final numerical grade $G_{final}$ would then be converted into a categorical clarity grade in step 110.

Figure 12:
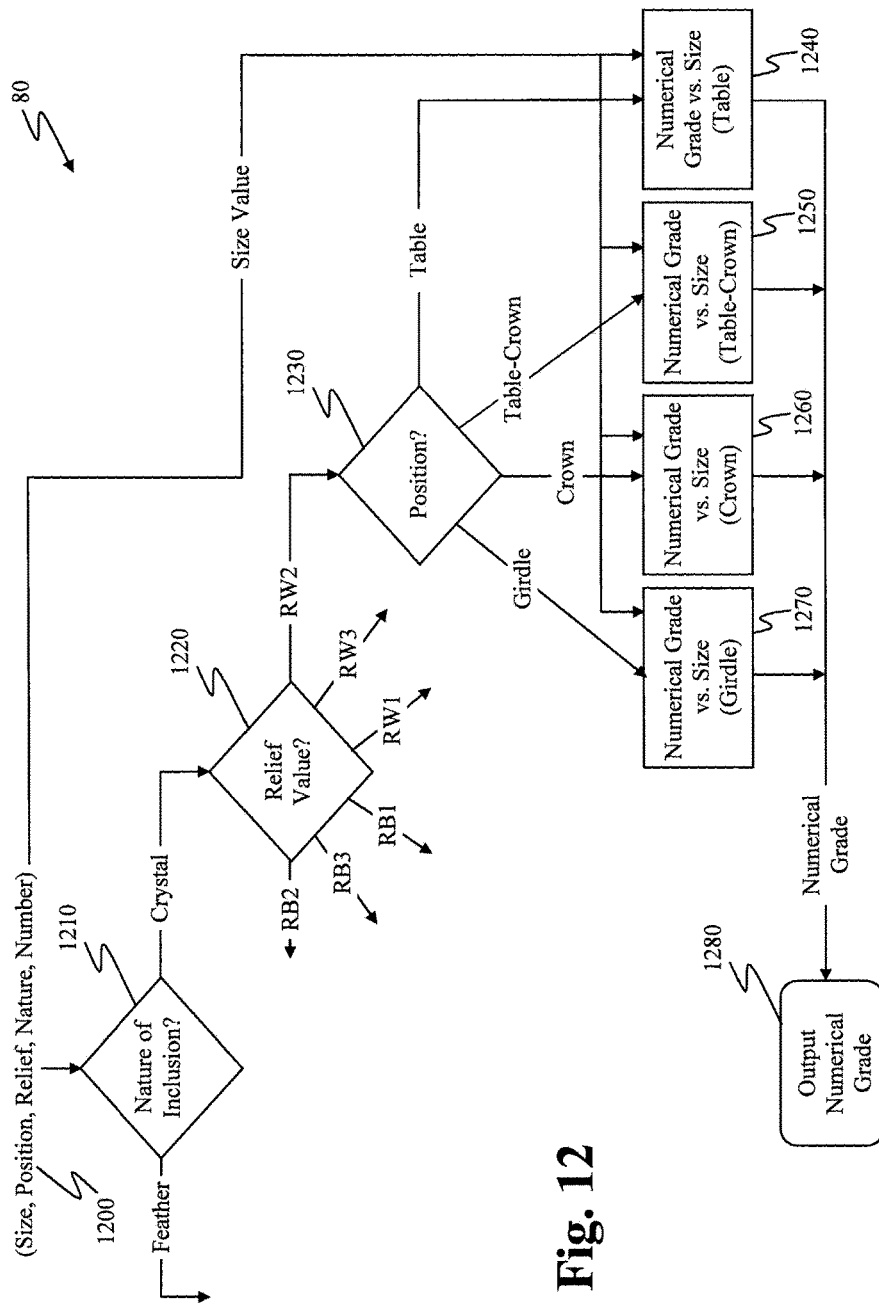
FIG. 12 is a simplified diagram illustrating a process for identifying look up tables/curves to which inclusion parameters for a gem are applied in order to obtain a clarity grade for the gem in accordance with an embodiment of the present invention.

Referring to FIG. 12, one possible sequence of operations is illustrated for implementing step 80 of FIG. 1 in accordance with an embodiment of the present invention. The operations of step 80 involve identifying look up tables/curves to which inclusion parameters for a gem are applied in order to obtain a numerical clarity grade for the gem. Following the inputting of inclusion parameter values at 1200, step 1210 thereafter queries the received inclusion parameter values to identify whether the type of the inclusion is a crystal or a feather. For the example diamond being considered, the type is indicated to be "crystal", therefore step 1220 would next be accessed to identify the relief value.

In step 1220, there are six (6) possible relief values shown for this example, three for White Reliefs—RW1, RW2, and RW3—and three for Black Reliefs—RB1, RB2, and RB3. For the diamond being considered, RW2 has been received as relief value, therefore step 1230 would next be accessed to identify the position value.

In step 1230, depending upon the position value received, the processing would be routed to a Numerical Grade Versus Size block 1240 for Table regions, a Numerical Grade Versus Size block 1250 for Table-Crown regions, a Numerical Grade Versus Size block 1260 for Crown regions, or a Numerical Grade Versus Size block 1270 for Girdle regions, for further processing. Each of these blocks 1240 to 1270 also receives the relative size value from the input inclusion values at 1200, and each has a look-up table or executes a mathematical model relating relative size to clarity grades. For example, block 1240 can implement a look-up table or execute a mathematical model corresponding to an equation such as shown in FIG. 11A or 11B, as discussed above, which relates relative size to clarity grades for crystals, in the Table region, with relief values of RW2. At step 1280, the determined numerical Clarity Grade is output for processing by step 100 of FIG. 1. One of ordinary skill in the art would understand that FIG. 12 illustrates a progression of processing for one combination of the inclusion parameters, and would understand from FIG. 12 how to implement similar progressions of processing for other combinations of inclusion parameters.

For the diamond being considered, the position value is "Crown", therefore block 1260 would be accessed, which would implement a look-up table or execute a mathematical model similar to the equation shown in FIG. 11A, but which relates relative size to clarity grades for crystals, in the Crown region, with relief values of RW2. Although the plots in FIG. 9 do not set forth the ultimate models/equations determined for the plotted values (such as in FIGS. 11A and 11B), the plots do provide some indication of the Clarity Grade values that may be predicted by the ultimate models/ equations. Referring specifically to the Crown Plot 920, it can be seen that the plot relates to inclusions that are crystals having an RW2 relief value and located in the Crown region. For the diamond being considered, the relative size value was determined to be 28. Applying this relative size value to Crown Plot 920, it can be seen that a Clarity Grade in the VS2 range would be returned. This is in agreement with the Clarity Grade of VS2 that appears in FIG. 7 for diamond number 140912101.

It is to be understood that in the preferred embodiment of the invention, a numerical Clarity Grade would be returned by step 80 of FIG. 1 (see step 1280 of FIG. 12) and then further processed, as described above, in step 100 to apply adjustments based upon the number of reflections or additional inclusions in the gem being graded, and converted in step 110 to a categorical (or parameterized) Clarity Grade.

The present invention has been described above with reference to several different embodiments. However, those skilled in the art will recognize that changes and modifications may be made in the above described embodiments without departing from the scope and spirit of the invention. Furthermore, while the present invention has been described in connection with a specific processing flow, those skilled in the art will recognize that a large amount of variation in configuring the processing tasks and in sequencing the processing tasks may be directed to accomplishing substantially the same functions as are described herein. These and other changes and modifications which are obvious to those skilled in the art in view of what has been described herein are intended to be included within the scope of the present invention.

What is claimed is:

1. A non-transitory computer-readable medium including one or more sequences of instructions that, when executed by one or more processors, cause the processors to perform operations comprising:
   receiving pixelated image data for a plurality of gems, wherein the image data for each gem includes an overall gem image and any inclusion within the overall gem image;
   mapping the inclusions within the pixelated image data of each gem by counting a number of pixels in the image data of the inclusions;
   calculating an ellipse to approximate the inclusions within the image data for each gem;
   calculating a size of each gem using a number of pixels in the image data of the gem;
   parameterizing locations of the mapped inclusions within the pixelated image data of each gem;
   deriving a mathematical ratio between an ellipse of a particular inclusion and the size of the corresponding gem; and
   assigning a derived clarity grade to each gem as a function of the mathematical ratio relationship and a parameterized location for each inclusion location, for each inclusion.

2. The non-transitory computer-readable medium of claim 1, further comprising a sub-module for removing outlier portions of the parameter data so as to provide a data subset, and wherein a mathematical relationship is derived from the data subset.

3. The non-transitory computer readable medium of claim 1, wherein the parameterized locations are at least one of pavilion, girdle, crown, table-crown, and table.

4. The non-transitory computer readable medium of claim 1, further comprising, determining a relief parameter for each inclusion in each gem using a pixel histogram of an identified inclusion and a pixel histogram of an area proximate to each inclusion.

5. The non-transitory computer readable medium of claim 4, wherein the determining a derived clarity grade includes a relief parameter.

6. A non-transitory computer-readable medium including one or more sequences of instructions that, when executed by one or more processors, cause the processors to perform operations comprising:
   receiving pixelated image data for a plurality of gems, wherein the image data for each gem includes an overall gem image and any inclusion within the overall gem image;
   parameterizing locations of the mapped inclusions within the pixelated image data of each gem;
   mapping each of the parameterized locations to images of the gem;
   inputting the parameterized locations for each of the plurality of inclusion characteristics into a mathematical formula; and
   determining a parameterized clarity grade for the gem, wherein the parameterized clarity grade based on the mathematical formula.

7. The non-transitory computer readable medium of claim 6, wherein the parameterized locations are at least one of pavilion, girdle, crown, table-crown, and table.

8. The non-transitory computer readable medium of claim 6, further comprising, determining a relief parameter for each inclusion in each gem using a pixel histogram of an identified inclusion and a pixel histogram of an area proximate to each inclusion.

9. The non-transitory computer readable medium of claim 8, wherein the determining a derived clarity grade includes a relief parameter.

* * * * *

UNITED STATES PATENT AND TRADEMARK OFFICE
CERTIFICATE OF CORRECTION

PATENT NO. : 10,318,515 B2
APPLICATION NO. : 15/151902
DATED : June 11, 2019
INVENTOR(S) : Verboven et al.

Page 1 of 1

It is certified that error appears in the above-identified patent and that said Letters Patent is hereby corrected as shown below:

On the Title Page

(72) Inventor:
Add Third Inventor:
Dirk Nuyts, Dr Vande Perrestraat (BE);

Signed and Sealed this
Eleventh Day of August, 2020

Andrei Iancu
*Director of the United States Patent and Trademark Office*